(12) United States Patent
Hoffmann et al.

(10) Patent No.: US 9,555,110 B2
(45) Date of Patent: Jan. 31, 2017

(54) ANTI-ALPHA-V INTEGRIN ANTIBODY FOR THE TREATMENT OF PROSTATE CANCER

(75) Inventors: Axel Hoffmann, Wehrheim (DE); Heinrich Lannert, Schwetzingen (DE); Klaus Brischwein, Munich (DE); Frederic Christian Pipp, Gruendau (DE); Juergen Reindl, Rossdorf (DE); Karin Groll, Muehltal (DE); Michael Zuehlsdorf, Darmstadt (DE); Otmar Pfaff, Frankfurt am Main (DE); Sabine Raab, Rosbach (DE); Ulrike Dau, Darmstadt (DE); Benoit Destenaves, Peron (FR)

(73) Assignee: Merck Patent GmbH, Darmstadt (DE)

( * ) Notice: Subject to any disclaimer, the term of this patent is extended or adjusted under 35 U.S.C. 154(b) by 201 days.

(21) Appl. No.: 13/984,669

(22) PCT Filed: Feb. 7, 2012

(86) PCT No.: PCT/EP2012/000548
§ 371 (c)(1),
(2), (4) Date: Oct. 28, 2013

(87) PCT Pub. No.: WO2012/107211
PCT Pub. Date: Aug. 16, 2012

(65) Prior Publication Data
US 2014/0086908 A1    Mar. 27, 2014

(30) Foreign Application Priority Data
Feb. 11, 2011 (EP) .................................... 11001135

(51) Int. Cl.
| | | |
|---|---|---|
| *A61K 38/00* | (2006.01) | |
| *A61K 39/395* | (2006.01) | |
| *C07K 16/28* | (2006.01) | |
| *C07K 16/30* | (2006.01) | |
| *A61K 45/06* | (2006.01) | |
| *A61K 39/00* | (2006.01) | |

(52) U.S. Cl.
CPC ......... *A61K 39/39558* (2013.01); *A61K 45/06* (2013.01); *C07K 16/2848* (2013.01); *C07K 16/3069* (2013.01); *A61K 2039/505* (2013.01); *A61K 2039/545* (2013.01); *C07K 2317/24* (2013.01); *C07K 2317/76* (2013.01)

(58) Field of Classification Search
None
See application file for complete search history.

(56) References Cited

U.S. PATENT DOCUMENTS

| | | | |
|---|---|---|---|
| 5,753,230 A | 5/1998 | Brooks et al. | |
| 5,766,591 A | 6/1998 | Brooks et al. | |
| 5,985,278 A * | 11/1999 | Mitjans et al. | ............ 424/143.1 |
| 7,550,142 B2 * | 6/2009 | Giles-Komar et al. | .... 424/133.1 |
| 8,420,348 B2 | 4/2013 | Goodman et al. | |
| 8,562,986 B2 | 10/2013 | Goodman et al. | |
| 9,008,388 B2 | 4/2015 | Yoshioka et al. | |
| 2006/0002007 A1 | 1/2006 | Lee et al. | |
| 2007/0025889 A1 | 2/2007 | Boggs et al. | |
| 2010/0254977 A1* | 10/2010 | Goodman et al. | ......... 424/133.1 |
| 2012/0263739 A1 | 10/2012 | Langer et al. | |
| 2013/0203079 A1 | 8/2013 | Goodman et al. | |
| 2014/0086908 A1 | 3/2014 | Hoffmann et al. | |

FOREIGN PATENT DOCUMENTS

| | | |
|---|---|---|
| DE | 102005062440 A1 | 7/2007 |
| EP | 0531472 A1 | 3/1993 |
| EP | 0770622 B1 | 2/2000 |
| EP | 719859 B1 | 7/2003 |
| EP | 1362868 A2 | 11/2003 |
| EP | 2706358 A2 | 3/2014 |
| WO | WO-98/52976 A1 | 11/1998 |
| WO | WO-00/15244 A3 | 6/2000 |
| WO | WO-00/34317 A3 | 8/2000 |
| WO | WO-02/69232 A3 | 2/2003 |
| WO | WO-03/053465 A2 | 7/2003 |
| WO | WO-2004/056308 A2 | 7/2004 |
| WO | WO-2005/016969 A2 | 2/2005 |
| WO | WO-2005/077414 A1 | 8/2005 |
| WO | WO-2007/001446 A3 | 3/2007 |
| WO | WO-2007/076950 A1 | 7/2007 |
| WO | WO-2008/008435 A2 | 1/2008 |
| WO | WO-2007/084670 A8 | 2/2008 |
| WO | WO-2009/010290 A2 | 1/2009 |

(Continued)

OTHER PUBLICATIONS

Brown et al. Tolerance of single, but not multiple, amino acid replacements in antibody VH CDR 2: a means of minimizing B cell wastage from somatic hypermutation? J. Immuno. May 1996, 3285-91.*

Vajdos et al. Comprehensive functional maps of the antigen-binding site of an anti-ErbB2 antibody obtained with shotgun scanning mutagenesis. J. Mol. Biol. Jul. 5, 2002, 320(2):415-28.*

Clinicaltrials.gov. A Study to Determine the Safety, Tolerability, Pharmacokinetics and Dynamic Effects of Different Doses of the Study Drug EMD 525797 in Prostate Cancer. Aug. 11, 2009-Dec. 20, 2010, p. 1-11.*

(Continued)

*Primary Examiner* — Maher Haddad
(74) *Attorney, Agent, or Firm* — Goodwin Procter LLP

(57) ABSTRACT

The invention is directed to the treatment of prostate cancer by means of antibodies. Above all, the invention relates to the administration of an anti-alpha-v integrin (receptor) antibody to patients suffering from prostate cancer, especially castration-resistant prostate cancer (CRPC), optionally accompanied by lymph node and bone tissue metastases (mCRPC). In particular, the invention relates to the therapy of said patients by means of the anti-angiogenic antibody DI17E6 and structural mutants thereof.

15 Claims, 9 Drawing Sheets

(56) References Cited

FOREIGN PATENT DOCUMENTS

Figure 1:
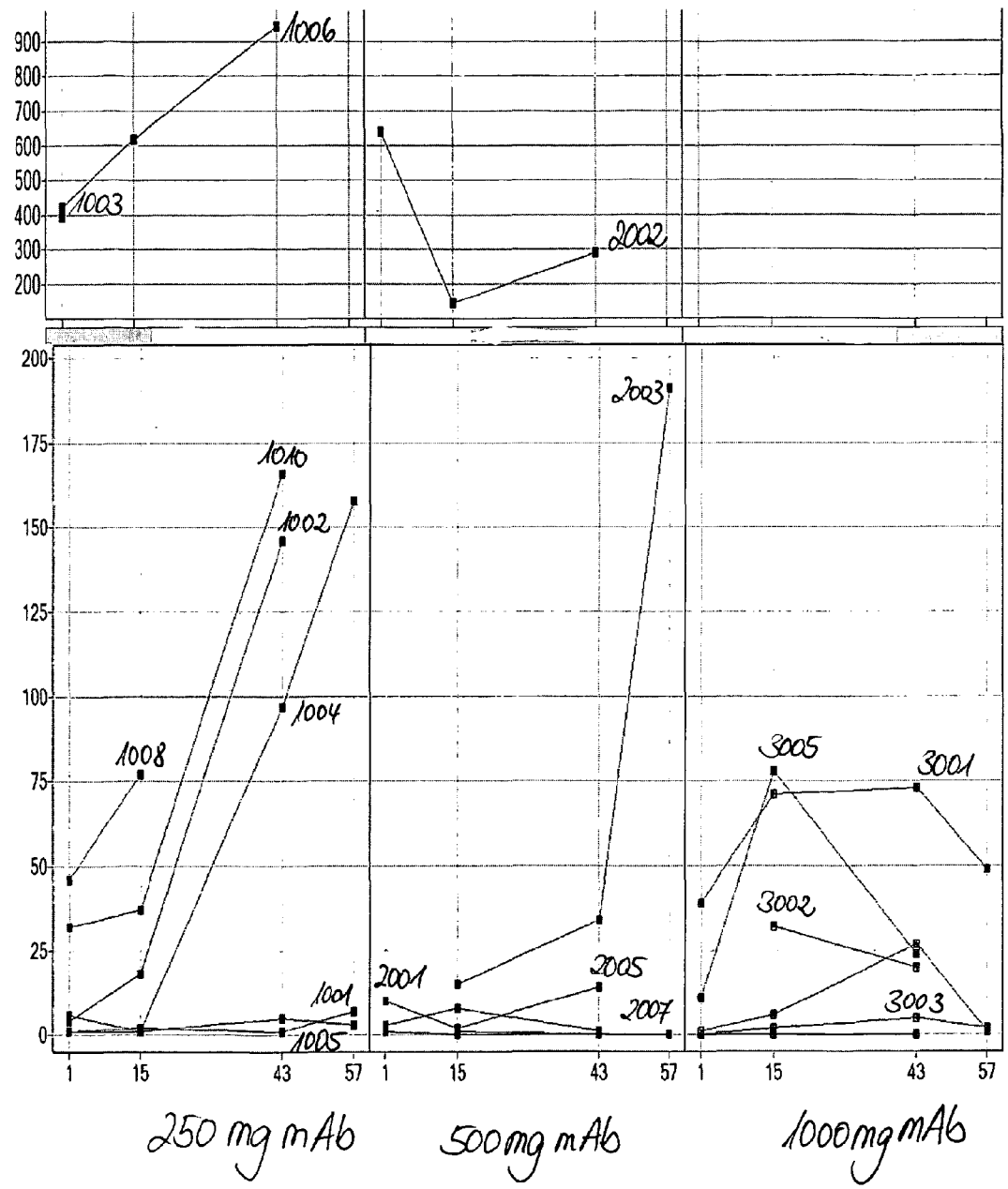

| WO | WO-2009/026328 | A2 | 2/2009 |
|---|---|---|---|
| WO | WO-2010/072348 | A1 | 7/2010 |
| WO | WO-2011/020529 | A2 | 2/2011 |
| WO | WO-2011/162933 | | 12/2011 |
| WO | WO-2014/143383 | A1 | 9/2014 |
| WO | WO-2015/035215 | A1 | 3/2015 |

OTHER PUBLICATIONS

"A study to determine the safety, tolerability, pharmacokinetics and dynamic effects of different doses of the study drug EM525797 in prostate cancer," clinicaltrials.gov, Aug. 11, 2009, 4 pages.

Bisanz et al. (2005) "Targeting ECM-Integrin Interaction with Liposome-Encapsulated Small Interfering RNAs Inhibits the Growth of Human Prostate Cancer in Bone Xenograft Imaging Model," *Molecular Therapy*, 12(4):634-643.

Desgrosellier et al. (2010) "Integrins in cancer: biological implications and therapeutic opportunities," *Nature Reviews Cancer*, 10(1):9-22 and corrigendum (1 page).

Nemeth et al. (2003) "Inhibition of $\alpha v\beta 3$ integrin reduces angiogenesis, bone turnover, and tumor cell proliferation in experimental prostate cancer bone metastases," *Clinical and Experimental Metastasis* 20(5):413-420.

Millard et al. (2011) "Integrin Targeted Therapeutics" *Theranostics*, 1:154-188.

"Product data sheet of Anti-Integrin alpha(v) (Ab-1) Mouse mAb (272-17E6) and corresponding safety data sheet," (2010) 6 pages.

Wagner et al. (2010) "Enhanced drug targeting by attachment of an anti $\alpha v$ integrin antibody to doxorubicin loaded human serum albumin nanoparticles," *Biomaterials* 31(8): 2388-2398.

Wirth et al. (2011) "A Phase 1 Study of DI17E6, an Antibody Targeting AV Integrins in Progressive Castrate-resistant Prostate Cancer with Bone Metastases (mCRPC) After Chemotherapy" *European J. Canc*, 47(supp. 1), 1 page.

Wirth et al. (2011) "A multicenter phase I study of DI17E6, a novel de-immunized monoclonal antibody to human $\alpha v$ integrins, in progressive castrate-resistant prostate cancer (CRPC) with bone metastases after chemotherapy" *J. Clin. Oncol* 29(15, suppl. E15060), 2 pages.

Anhorn MG et al., (2008) 'Specific Targeting of HER2 Overexpressing Breast Cancer Cells with Doxorubicin-Loaded Trastuzumab-Modified Human Serum Albumin Nanoparticles,' Bioconjug Chem, 19(12):2321-31.

Azare J et al., (2007), 'Constitutively Activated Stat3 Induces Tumorgenesis and Enhances Cell Motility of Prostate Epithelial Cells Through Integrin $\beta 6$,' Mol Cell Biol, 27(12):4444-53.

Boshart M et al., (1985), 'A Very Strong Enhancer is Located Upstream of an Immediate Early Gene of Human Cytomegalovirus,' Cell, 41(2):521-30.

Casset F et al., (2003), 'A Peptide Mimetic of an Anti-CD4 Monoclonal Antibody by Rational Design,' Biochem Biophys Res Commun, 307(1):198-205.

Chen Y et al., (1999) 'Selection and Analysis of an Optimized Anti-VEGF Antibody: Crystal Structure of an Affinity-Matured Fab in Complex with Antigen,' J Mol Biol, 293(4):865-81.

Chu FM et al., (2011) "A Phase 1, Multicenter, Open-Label Study of the Safety of Two Dose Levels of a Human Monoclonal Antibody to Human β(v) Integrins, Intetumumab, in Combination with Docetaxel and Prednisone in Patients with Castrate-Resistant Metastatic Prostate Cancer," Invest New Drugs, 29(4):674-9.

de Bono JS et al., (2008), 'Circulating Tumor Cells Predict Survival Benefit from Treatment in Metastatic Castration-Resistant Prostate Cancer,' Clin Cancer Res, 14(19):6302-9.

de Pascalis R et al., (2002), 'Grafting of "Abbreviated" Complementarity-Determining Regions Containing Specificity-Determining Residues Essential for Ligand Contact to Engineer a Less Immunogenic Humanized Monoclonal Antibody,' J Immunol, 169(6):3076-84.

Endo N et al., (1987) 'In vitro Cytotoxicity of a Human Serum Albumin-Mediated Conjugate of Methotrexate with Anti-MM46 Monoclonal Antibody,' Cancer Res, 47(4):1076-80.

Eskens FA et al., (2003) 'Phase I and Pharmacokinetic Study of Continuous Twice Weekly Intravenous Administration of Cilengitide (EMD 121974), a Novel Inhibitor of the Integrins $\alpha v\beta 3$ and $\alpha v\beta 5$ in Patients with Advanced Solid Tumours,' Eur J Cancer, 39(7):917-26.

Forsman ZH et al., (2004), 'Phylogenetic Analysis of Polyomavirus Simian Virus 40 from Monkeys and Humans Reveals Genetic Variation,' J Virol, 78(17):9306-16.

Gillies SD et al., (1998), 'Antibody-IL-12 Fusion Proteins are Effective in SCID Mouse Models of Prostate and Colon Carcinoma Metastases,' J Immunol, 160(12):6195-203.

Ilyinskii Po et al., (1992), 'Genetic Analysis of Simian Virus 40 From Brains and Kidneys of Macaque Monkeys,' J Virol, 66(11):6353-60.

International Search Report (Form ISA/210) for International Application No. PCT/EP2012/000548, mailed on May 23, 2012 (6 pages).

Kamizuru H et al., (2001), 'Monoclonal Antibody-Mediated Drug Targeting to Choroidal Neovascularization in the Rat,' Invest Ophthalmol Vis Sci, 42(11):2664-72.

Kawasaki K et al., (2001), 'Evolutionary Dynamics of the Human Immunoglobulin κ Locus and the Germline Repertoire of the Vκ Genes,' Eur J Immunol, 31(4):1017-28.

Krawinkel U and Rabbitts TH (1982), 'Comparison of the Hinge-Coding Segments in Human Immunoglobulin γ2 and γ4 Subclass Genes,' EMBO J, 1(4):403-7.

Lacal JC and Carnero A, (2003), 'Targeted Search for Anticancer Drugs—CNIO Cancer Conference. Mar. 16-18, Madrid, Spain,' IDrugs, 6(5):437-41.

Lamminmäki U and Kankare JA, (2001), 'Crystal Structure of a Recombinant Anti-Estradiol Fab Fragment in Complex with 17β-Estradiol,' J Biol Chem, 276(39):36687-94.

Lo KM et al., (1998), 'High Level Expression and Secretion of Fc-X Fusion Proteins in Mammalian Cells,' Protein Eng, 11(6):495-500.

Lo KM et al., (2005), 'Engineering a Pharmacologically Superior Form of Leptin for the Treatment of Obesity,' Protein Eng Des Sel, 18(1):1-10.

MacCallum RM et al., (1996), 'Antibody-Antigen Interactions: Contact Analysis and Binding Site Topography,' J Mol Biol, 262(5):732-45.

McCabe NP et al., (2007), 'Prostate Cancer Specific Integrin $\alpha v\beta 3$ Modulates Bone Metastatic Growth and Tissue Remodeling,' Oncogene, 26(42):6238-43.

Mitjans F et al., (1995), 'An Anti-α v-Integrin Antibody that Blocks Integrin Function Inhibits the Development of a Human Melanoma in Nude Mice,' J Cell Sci, 108(Pt 8):2825-38.

Padlan EA et al., (1989), 'Structure of an Antibody-Antigen complex: Crystal Structure of the HyHEL-10 Fab-Lysozyme Complex,' Proc Natl Acad Sci USA, 86(15):5938-42.

Rader C et al., (1998), 'A Phage Display Approach for Rapid Antibody Humanization: Designed Combinatorial V Gene Libraries,' Proc Natl Acad Sci USA, 95(15):8910-5.

Rudikoff S et al., (1982), 'Single Amino Acid Substitution Altering Antigen-Binding Specificity,' Proc Natl Acad Sci USA, 79(6):1979-83.

Scher HI et al., (2009), 'Circulating Tumor Cells as Prognostic Markers in Progressive, Castration-Resistant Prostate Cancer: A Reanalysis of IMMC38 Trial Data,' Lancet Oncol, 10(3):233-9.

Schäble KF et al., (1999), 'Characteristics of the Immunoglobulin Vκ Genes, Pseudogenes, Relics and Orphons in the Mouse Genome,' Eur J Immunol, 29(7):2082-6.

Simonsen CC and Levinson AD, (1983), 'Isolation and Expression of an Altered Mouse Dihydrofolate Reductase cDNA,' Proc Natl Acad Sci USA, 80(9):2495-9.

Strausberg RL et al., (2002), 'Generation and Initial Analysis of More than 15,000 Full-Length Human and Mouse cDNA Sequences,' Proc Natl Acad Sci USA, 99(26):16899-903.

Sutcliffe JG (1978), 'Nucleotide Sequence of the Ampicillin Resistance Gene *Escherichia coli* Plasmid pBR322,' Proc Natl Acad Sci USA, 75(8):3737-41.

(56) References Cited

OTHER PUBLICATIONS

Tucker GC (2006), 'Integrins: Molecular Targets in Cancer Therapy,' Curr Oncol Rep, 8(2):96-103.
Wirth M et al., (2013) 'A Multicenter Phase I Study of EMD 525797 (DI17E6), a Novel Humanized Monoclonal Antibody Targeting αv Integrins, in Progressive Castration-Resistant Prostate Cancer with Bone Metastases After Chemotherapy,' Eur Urol, 65(5):897-904.
Written Opinion (PCT Rule 43 bis.1) (Form ISA/237 with Form IB/373) for International Application No. PCT/EP2012/000548, mailed on May 23, 2012 (7 pages).
Wu H et al., (1999), 'Humanization of a Murine Monoclonal Antibody by Simultaneous Optimization of Framework and Cdr Residues,' J Mol Biol, 294(1):151-62.
Zheng DQ et al., (1999), 'Prostatic Carcinoma Cell Migration Via α(v)β3 Integrin is Modulated by Focal Adhesion Kinase Pathway,' Cancer Res, 59(7):1655-64.

* cited by examiner (B)

(A)

(B)

SEQUENCE LISTING

<160> NUMBER OF SEQ ID NOS: 7

<210> SEQ ID NO 1
<211> LENGTH: 214
<212> TYPE: PRT
<213> ORGANISM: Artificial Sequence
<220> FEATURE:
<223> OTHER INFORMATION: Description of Artificial Sequence: Synthetic polypeptide

```
<220> FEATURE:
<221> NAME/KEY: misc_feature
<222> LOCATION: (1)..(107)
<223> OTHER INFORMATION: Variable regions with the CRDs of the light
      chain
<220> FEATURE:
<221> NAME/KEY: misc_feature
<222> LOCATION: (24)..(34)
<223> OTHER INFORMATION: CDR1
<220> FEATURE:
<221> NAME/KEY: misc_feature
<222> LOCATION: (50)..(56)
<223> OTHER INFORMATION: CDR2
<220> FEATURE:
<221> NAME/KEY: misc_feature
<222> LOCATION: (89)..(97)
<223> OTHER INFORMATION: CDR3

<400> SEQUENCE: 1

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Ile Ser Asn Tyr
            20                  25                  30

Leu Ala Trp Tyr Gln Gln Lys Pro Gly Lys Ala Pro Lys Leu Leu Ile
        35                  40                  45

Tyr Tyr Thr Ser Lys Ile His Ser Gly Val Pro Ser Arg Phe Ser Gly
 50                  55                  60

Ser Gly Ser Gly Thr Asp Tyr Thr Phe Thr Ile Ser Ser Leu Gln Pro
 65                  70                  75                  80

Glu Asp Ile Ala Thr Tyr Tyr Cys Gln Gln Gly Asn Thr Phe Pro Tyr
                 85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 2
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (1)..(118)
<223> OTHER INFORMATION: Variable regions with the CDRs of the heavy
      chain
<220> FEATURE:
<221> NAME/KEY: misc_feature
<222> LOCATION: (31)..(35)
<223> OTHER INFORMATION: CDR1
```

```
<220> FEATURE:
<221> NAME/KEY: misc_feature
<222> LOCATION: (50)..(53)
<223> OTHER INFORMATION: CDR2
<220> FEATURE:
<221> NAME/KEY: misc_feature
<222> LOCATION: (99)..(107)
<223> OTHER INFORMATION: CDR3
<220> FEATURE:
<221> NAME/KEY: misc_feature
<222> LOCATION: (217)..(231)
<223> OTHER INFORMATION: IgG1 hinge region
<220> FEATURE:
<221> NAME/KEY: misc_feature
<222> LOCATION: (296)..(297)
<223> OTHER INFORMATION: Substitution within the IgG2 region

<400> SEQUENCE: 2

Gln Val Gln Leu Gln Gln Ser Gly Gly Glu Leu Ala Lys Pro Gly Ala
  1               5                  10                  15

Ser Val Lys Val Ser Cys Lys Ala Ser Gly Tyr Thr Phe Ser Ser Phe
             20                  25                  30

Trp Met His Trp Val Arg Gln Ala Pro Gly Gln Gly Leu Glu Trp Ile
         35                  40                  45

Gly Tyr Ile Asn Pro Arg Ser Gly Tyr Thr Glu Tyr Asn Glu Ile Phe
 50                  55                  60

Arg Asp Lys Ala Thr Met Thr Thr Asp Thr Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Ser Phe Leu Gly Arg Gly Ala Met Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Cys Ser Arg Ser Thr Ser Glu Ser Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Asn Phe Gly Thr Gln Thr Tyr Thr Cys Asn Val Asp His Lys Pro Ser
        195                 200                 205

Asn Thr Lys Val Asp Lys Thr Val Glu Pro Lys Ser Ser Asp Lys Thr
    210                 215                 220

His Thr Cys Pro Pro Cys Pro Ala Pro Pro Val Ala Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Ala Gln Ser Thr Phe Arg Val Val Ser
    290                 295                 300

Val Leu Thr Val Val His Gln Asp Trp Leu Asn Gly Lys Glu Tyr Lys
305                 310                 315                 320
```

```
Cys Lys Val Ser Asn Lys Gly Leu Pro Ala Pro Ile Glu Lys Thr Ile
            325                 330                 335

Ser Lys Thr Lys Gly Gln Pro Arg Glu Pro Gln Val Tyr Thr Leu Pro
        340                 345                 350

Pro Ser Arg Glu Glu Met Thr Lys Asn Gln Val Ser Leu Thr Cys Leu
    355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Met Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly Lys
        435                 440                 445

<210> SEQ ID NO 3
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 3

Glu Pro Lys Ser Ser Asp Lys Thr His Thr Cys Pro Pro Cys Pro
1               5                   10                  15

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (6)..(6)
<223> OTHER INFORMATION: Position may be mutated

<400> SEQUENCE: 4

Trp Gly Gln Gly Thr Ser Val Thr Val Ser Ser
1               5                   10

<210> SEQ ID NO 5
<211> LENGTH: 30
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (9)..(9)
<223> OTHER INFORMATION: Position may be mutated
<220> FEATURE:
<221> NAME/KEY: misc_feature
<222> LOCATION: (13)..(13)
<223> OTHER INFORMATION: Position may be mutated
<220> FEATURE:
<221> NAME/KEY: misc_feature
<222> LOCATION: (20)..(20)
<223> OTHER INFORMATION: Position may be mutated

<400> SEQUENCE: 5
```

```
Gln Val Gln Leu Gln Gln Ser Gly Ala Glu Leu Ala Glu Pro Gly Ala
1               5                   10                  15

Ser Val Lys Met Ser Cys Lys Ala Ser Gly Tyr Thr Phe Ser
            20                  25                  30
```

<210> SEQ ID NO 6
<211> LENGTH: 14
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: misc_feature
<222> LOCATION: (3)..(3)
<223> OTHER INFORMATION: Position may be mutated
<220> FEATURE:
<221> NAME/KEY: misc_feature
<222> LOCATION: (5)..(5)
<223> OTHER INFORMATION: Position may be mutated

<400> SEQUENCE: 6

```
Trp Val Lys Gln Arg Pro Gly Gln Gly Leu Glu Trp Ile Gly
1               5                   10
```

<210> SEQ ID NO 7
<211> LENGTH: 32
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: misc_feature
<222> LOCATION: (6)..(6)
<223> OTHER INFORMATION: Position may be mutated
<220> FEATURE:
<221> NAME/KEY: misc_feature
<222> LOCATION: (10)..(10)
<223> OTHER INFORMATION: Position may be mutated
<220> FEATURE:
<221> NAME/KEY: misc_feature
<222> LOCATION: (16)..(16)
<223> OTHER INFORMATION: Position may be mutated
<220> FEATURE:
<221> NAME/KEY: misc_feature
<222> LOCATION: (19)..(19)
<223> OTHER INFORMATION: Position may be mutated
<220> FEATURE:
<221> NAME/KEY: misc_feature
<222> LOCATION: (21)..(21)
<223> OTHER INFORMATION: Position may be mutated
<220> FEATURE:
<221> NAME/KEY: misc_feature
<222> LOCATION: (25)..(25)
<223> OTHER INFORMATION: Position may be mutated

<400> SEQUENCE: 7

```
Lys Ala Thr Met Thr Ala Asp Thr Ser Ser Ser Thr Ala Tyr Met Gln
1               5                   10                  15

Leu Ser Gly Leu Thr Ser Glu Asp Ser Ala Val Tyr Tyr Cys Ala Ser
            20                  25                  30
```

ANTI-ALPHA-V INTEGRIN ANTIBODY FOR THE TREATMENT OF PROSTATE CANCER

CROSS-REFERENCE TO RELATED APPLICATIONS

This application is the U.S. national stage of international patent application PCT/EP2012/000548, filed Feb. 7, 2012, which claims the benefit of and priority to EP Patent Application No. 11001135.0, filed on Feb. 11, 2011.

SEQUENCE LISTING

The instant application contains a Sequence Listing which has been submitted in ASCII format via EFS-Web and is hereby incorporated by reference in its entirety. Said ASCII copy, created on Oct. 28, 2013, is named MRK-009_SL.txt and is 9,721 bytes in size.

Please delete the paragraph on page 10, lines 6-13 and replace it with the following paragraph; please note that the underlined amino acid residues in the FR1, FR2, FR3, and FR4 sequences are not underlined to show amendments but are underlined as originally appearing in the specification for emphasis; only the sequence identifiers have been amended:

The respective use of DI17E6 antibody, comprising one or more modifications within the heavy chain framework regions FR1: QVQLQQSGAELAEPGASVKMSCKASGYTFS (SEQ ID No. 5)

FR2: WVKQRPGQGLEWIG (SEQ ID No. 6)

FR3: KATMTADTSSSTAYMQLSGLTSEDSAVYYCAS (SEQ ID No. 7)

FR4: WGQGTSVTVSS, (SEQ ID No. 4)

wherein one or more of the bold and underlined positions are mutated and are different compared to the original respective sequence.

Please delete the paragraph on page 13, line 23 to page 14, line 3 and replace it with the following paragraph; please note that the underlined amino acid residues in the FR1, FR2, FR3, and FR4 sequences are not underlined to show amendments but are underlined as originally appearing in the specification for emphasis; only the sequence identifiers have been amended:

However, as it was shown in WO 2009/010290, also variants of DI17E6 can be used according to the teaching of this invention. Thus, DI17E6 variants comprising one or more modifications within the heavy chain framework regions FR1: QVQLQQSGAELAEPGASVKMSCKASGYTFS (SEQ ID No. 5)

FR2: WVKQRPGQGLEWIG (SEQ ID No. 6)

FR3: KATMTADTSSSTAYMQLSGLTSEDSAVYYCAS (SEQ ID No. 7)

FR4: WGQGTSVTVSS, (SEQ ID No. 4)

wherein one or more of the bold and underlined positions are mutated, can be used in the treatment of prostate cancer patients as described. In more detail, the following position heavy chain framework region is mutated at one, more or all of the following positions can be mutated: A9, E13, M20, K38, R40, A72, S76, Q82, G85, T87, S91 and S113. These variants show the same or very similar biological activity and efficacy as compared to DI17E6 defined by its sequences above.

FIELD OF THE INVENTION

The invention is directed to the treatment of prostate cancer by means of antibodies. Above all, the invention relates to the administration of an anti-alpha-v integrin (receptor) antibody to patients suffering from prostate cancer, especially castration-resistant prostate cancer (CRPC) without or after chemotherapy, optionally accompanied by lymph node and bone tissue metastases (mCRPC). In particular, the invention relates to the therapy of said patients by means of the anti-angiogenic antibody DI17E6 and structural mutants thereof.

BACKGROUND OF THE INVENTION

Prostate cancer is the most commonly occurring cancer aside skin cancer in the US, and is the second most common cause of male cancer deaths.

Prostate cancer is classified in four stages: Stage I prostate cancer is found in the prostate only and cannot be felt during a digital rectal exam nor is it visible by imaging. In stage II prostate cancer, the tumor has grown inside the prostate but has not extended beyond it, whereas in stage III, the cancer has spread outside the prostate, but to a minimal extent only. Often, prostate cancer in stage III will have spread only to nearby tissues, such as the seminal vesicles. Finally, in stage IV, the cancer has spread outside the prostate to other tissues, such as the lymph nodes, bones, liver, and/or lungs or brain.

The spectrum of prostate cancers that are progressing despite castrate levels of testosterone includes tumors that have shown varying degrees and durations of response to primary hormone treatment, and clinical manifestations that range from a rising prostate-specific antigen (PSA) alone, a rising PSA with osseous and/or soft-tissue spread, or a predominantly visceral disease pattern.

Currently approved treatment of prostate cancer includes surgical castration, chemical castration, or a combination of surgical and chemical castration. Removal of the testes, the primary testosterone producing organ, reduces the levels of circulating androgens, to less than 5% of normal levels. This reduction in androgen levels inhibits prostate tumor growth. Although the anti-tumor effects of surgical castration are direct, the anti-tumor effects can be temporary. Surgical castration often leads to clonal selection of androgen-independent prostate tumor cells. This results in re-growth of the prostate tumor in a form that proliferates without testosterone or DHT Stimulation. Chemical castration (also called medical castration) is often substituted for surgical castration, as an initial treatment. Despite its high prevalence, treatment options for men having prostate cancer remain relatively limited and typically depend on the stage of the cancer.

Treatment options include surgical treatments such as radical prostatectomy, in which the prostate is completely removed and radiation, applied through an external beam that directs the dose to the prostate from outside the body or via low-dose radioactive seeds that are implanted within the prostate to kill cancer cells locally. Anti-androgen hormone therapy also is used in the treatment of prostate cancer, either alone or in conjunction with surgery or radiation. Hormone therapy typically aims at blocking the pituitary from producing hormones that stimulate testosterone production by use of castration or administration of hormone analogs and requires that patients have injections of these hormone analogs for protracted periods. Finally, chemotherapeutic approaches have been used to treat advanced prostate cancer, usually as a last resort when other approaches have failed. Since a couple of years, the combination of docetaxel and prednisone was established as the new standard of care for patients who have progressed on androgen deprivation.

None of the treatments described above are curative and prostate cancer being androgen dependent at first, often will progress despite surgical and hormonal-based therapies, and become resistant over time, leading to a cancer type which is called "hormone refractory cancer" or "castration resistant cancer" (CRPC).

Clinical disease manifestations of CRPC are commonly related to bone metastases and may include pain, pathologic fractures, and spinal cord compression, with local recurrences that may be associated with pelvic discomfort, renal dysfunction due to ureteral compression, bladder outlet obstruction, and sexual dysfunction. Further, while bone cancer is the predominant result of CRPC, patients may develop soft-tissue metastases (lymph node(s)) and visceral metastasis in liver, lung, brain, and other organs. Patients with CRPC are minimally responsive to chemotherapy and the majority of patients die due to progressive prostate cancer within 20 months of initiating treatment. Bisphosphonates are commonly used in patients with castrate-resistant prostate cancer who have bone metastases.

It has been shown that prostate tumors remain dormant and clinically undetectable until they begin to secrete angiogenic factors and down-regulate the expression of angiogenic inhibitors. In general, it can be stated that angiogenesis is critical to the genesis of prostate tumors. Therefore, it was not completely surprising that anti-angiogenic agents inhibit prostate cancer cell growth.

In prostate cancer, tumor cells express an abnormal integrin repertoire and are surrounded by a markedly aberrant extracellular matrix (ECM). These changes have profound consequences, given the ability of each integrin to regulate specific cell functions. Expression of β3 and β1 subunits activates specific signaling pathways and support distinct cancer cell functions. β3 is uniquely required in cancer cells for increasing cdc2 levels as well as cdc2 kinase activity. These effects are specific for β3 and are not observed for β6. Up-regulation of β3 and β6 integrin variants has been described. Zheng et al. (Cancer Research 1999; 59, 1655-1664) used human prostate cancer cells isolated from sixteen surgical specimens, to show that these cells express αvβ3, whereas normal prostate epithelial cells do not. Similarly, αvβ6 was found to be expressed in adenocarcinoma (Li et al.; Molecular and Cellular Biology 2007; 27, 4444).

The use of integrin inhibitors is likely to affect both cancer cell survival and angiogenesis since integrins are expressed by tumor cells as well as by endothelial cells. Although it is hard to discriminate between an effect on tumor growth and an effect on angiogenesis, a maximal response of these inhibitors can be predicted when the targeted integrin is expressed by both tumor and endothelial cells.

Bone is the most frequent metastatic site for prostate cancer. Bisanz et al. (Molecular Therapy 2005; 12, 634-643) illustrate a positive role for alpha-v integrins on prostate tumor survival in the bone. Analysis of human prostate cancer bone xenografts shows that intratumoral administration of liposome encapsulated human alpha-v siRNAs significantly inhibits the growth of PC3 tumors in bone and increases apoptosis of prostate tumor cells. Further studies (McCabe et al., Oncogene 2007; 26, 6238-6243) demonstrate that αvβ3 integrin activation on tumor cells is essential for the recognition of key bone specific matrix proteins. These data suggest that the αvβ3 integrin modulates prostate cancer growth in distant metastasis.

Since integrins mediate the interactions between tumor cells and bone microenvironment and facilitate growth in bone, a potential application of the use of integrin inhibitors is to prevent prostate cancer bone lesions. These lesions are osteoblastic and/or osteolytic and are frequently detected in prostate cancer patients (over 80% of prostate cancer patients have established bone metastasis at autopsy).

A recent study has shown that the αvβ3 integrin promotes bone gain mediated by prostate cancer cells that metastasize to the bone and point to αvβ3 as a potential therapeutic target to block prostate cancer osteoblastic lesions. Immunohistochemical analysis has demonstrated the presence of αv integrin in a large proportion of human prostate cancer tissues samples.

These and other results suggest that anti-integrin agents may have both direct and indirect antitumor activity. But there are only few clinical trials reporting that peptide or non-peptide integrin inhibitors are effective agents in prostate cancer therapy.

Therefore, there is a need to provide a potent anti-integrin agent for use in the therapy of prostate cancer, especially castration-resistant prostate cancer developing bone metastases.

SUMMARY OF THE INVENTION

It has been found by the inventors that the known monoclonal anti-alpha v antibody DI-17E6 (designated herein also as EMR62242 or EMD 525797) is highly effective in (i) a monotherapy based clinical setting and (ii) in a combinatorial clinical setting together with hormonal agents and/or chemotherapeutic agents and/or tyrosine kinase inhibitors or other angiogenesis inhibitors in the treatment of prostate cancer.

Figure 3:
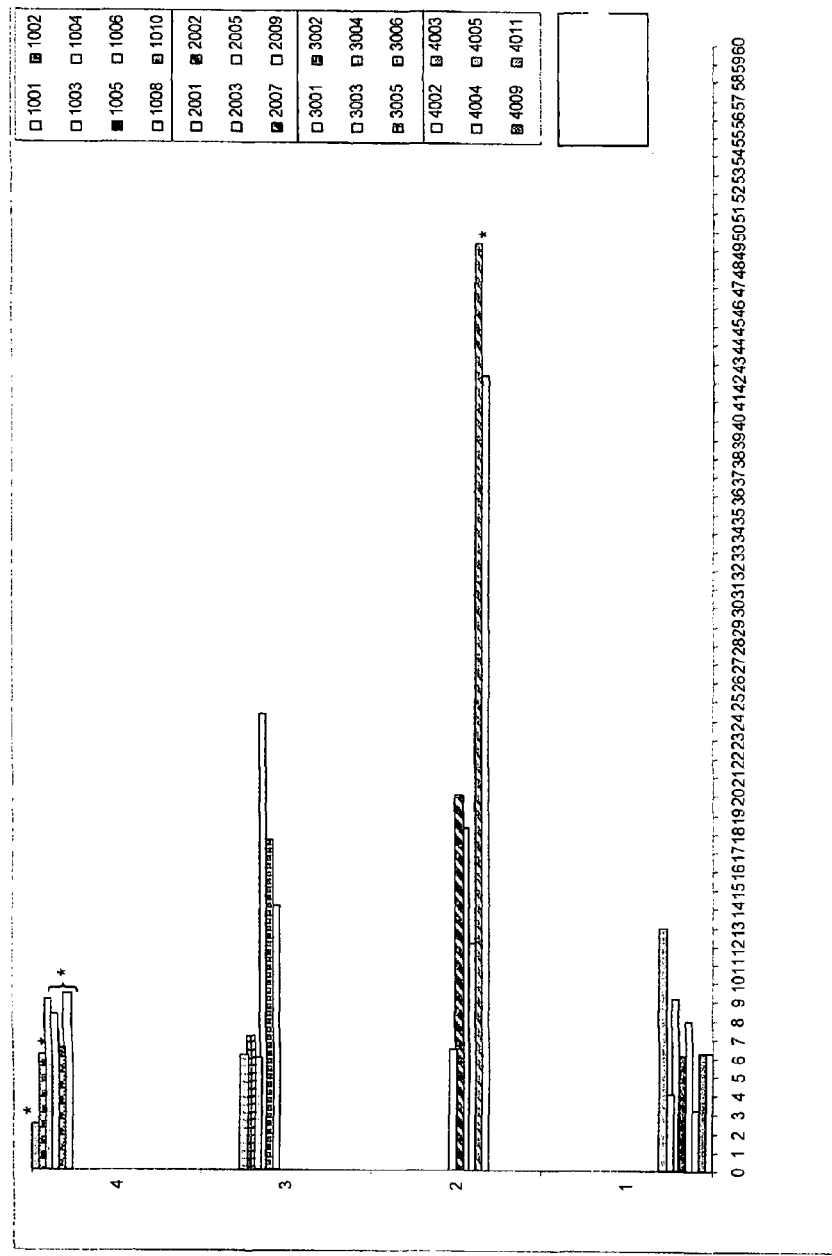

In a first aspect of the invention, it was shown in clinical trials that the known specifically engineered hybrid monoclonal anti-alpha-v antibody DI17E6 is well tolerated in prostate tumor patients without significant side effects at doses of at least 500 mg mAb each two weeks administered by infusion during a treatment period of at least four months (FIG. 3, Table 3).

In a second aspect of the invention it was shown, when administering DI17E6 with doses of at least 500 mg each two weeks is effective in the treatment of prostate cancer, preferably castrate-resistant prostate cancer (CRPC). As a result, the number of prostate derived circulating tumor cells (CTC) in the blood of these patients can be significantly reduced within the treatment period, above all if this number was originally (at the beginning of the treatment) very high (FIG. 1).

Figure 4:
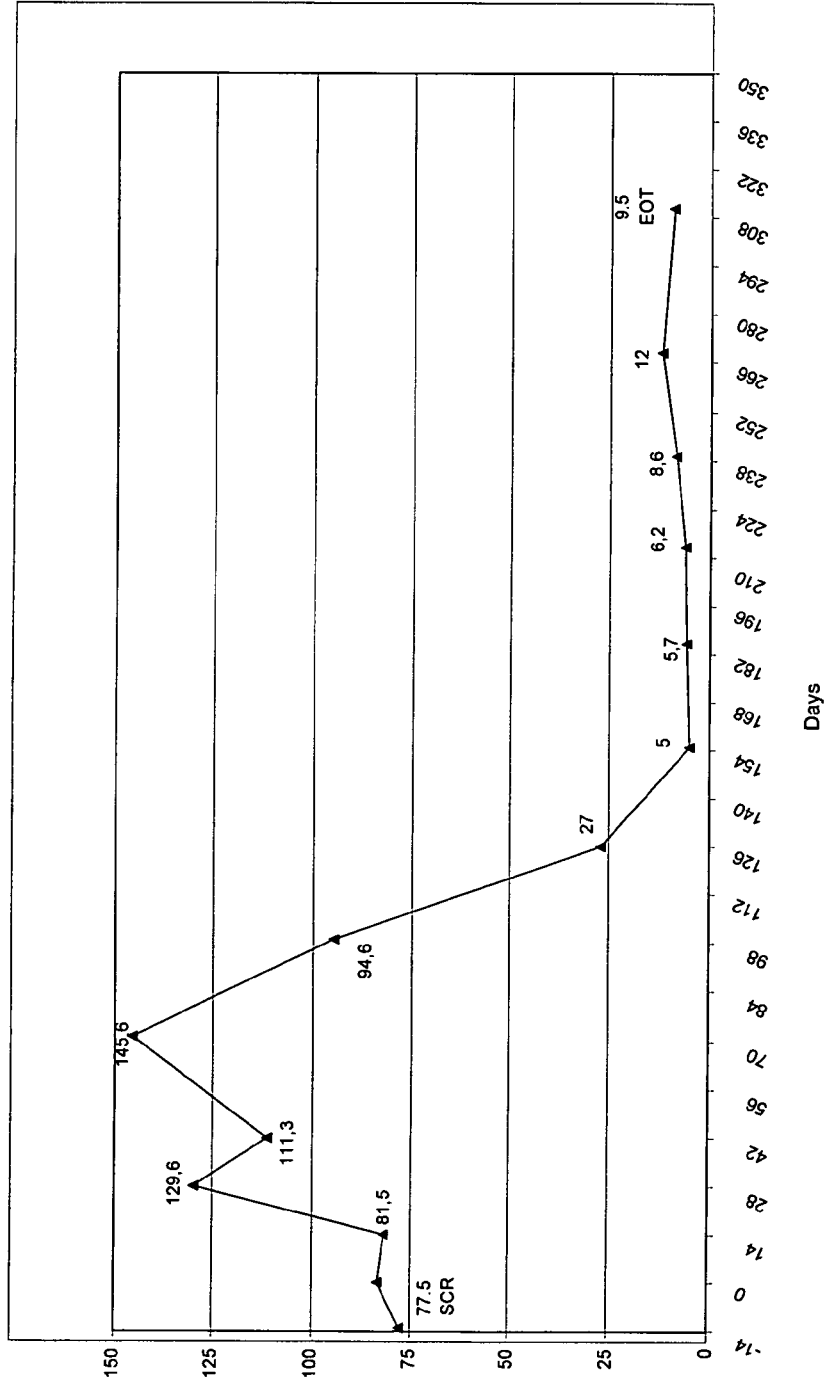
Figure 4:
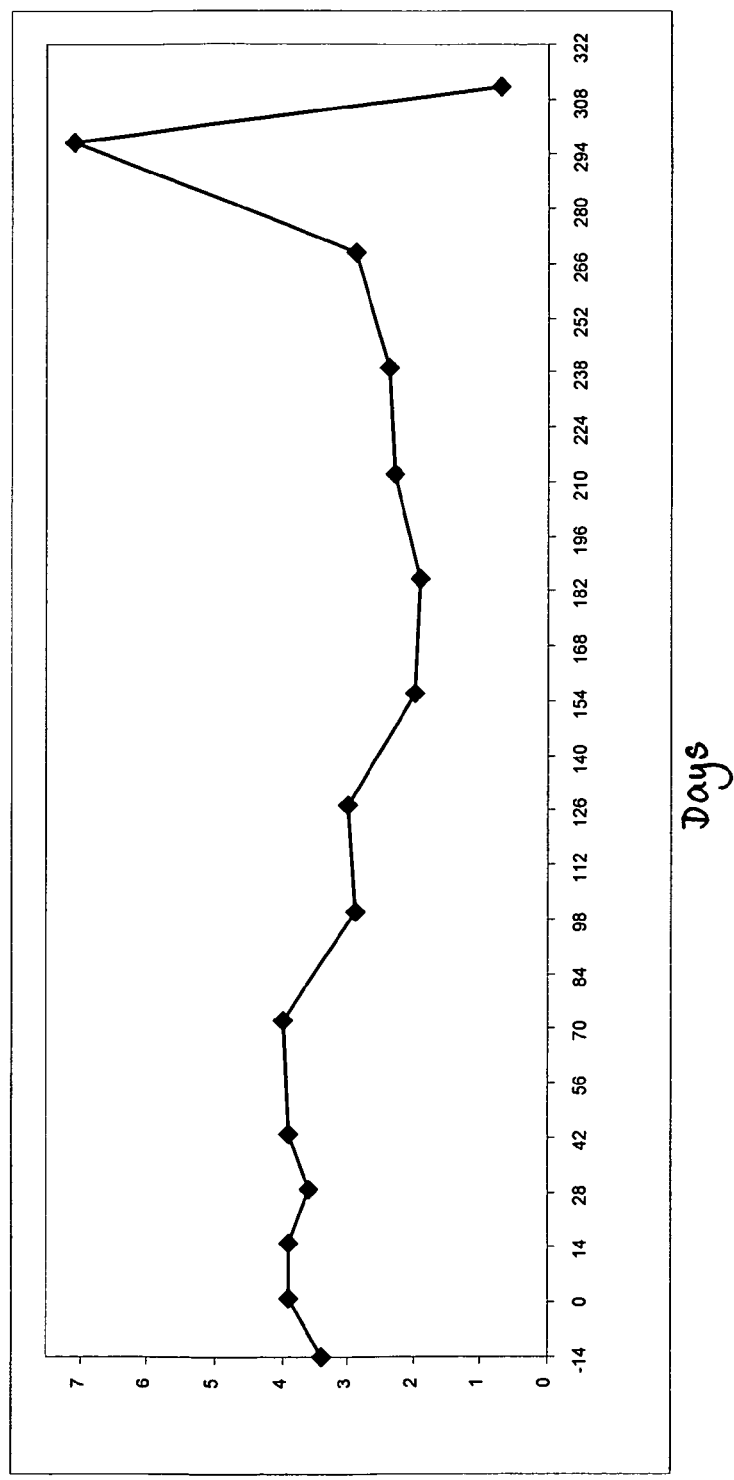
Figure 5:
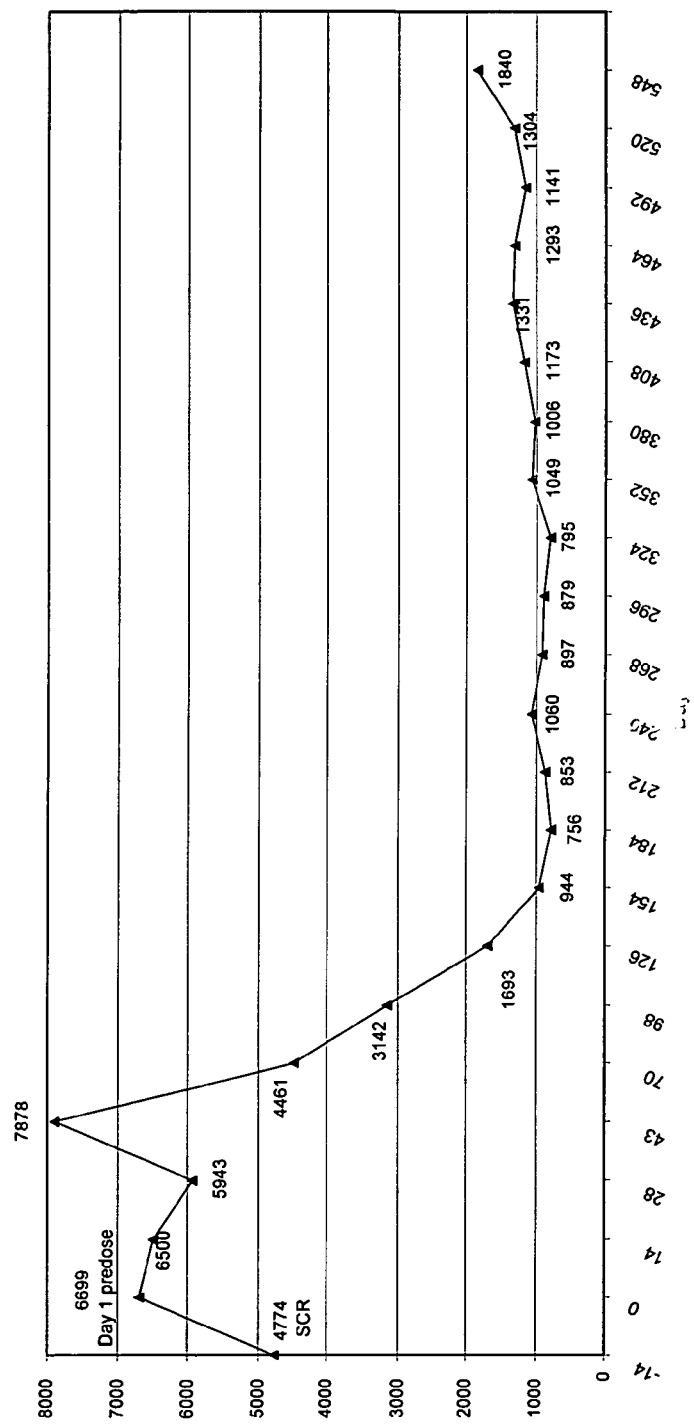
Figure 5:
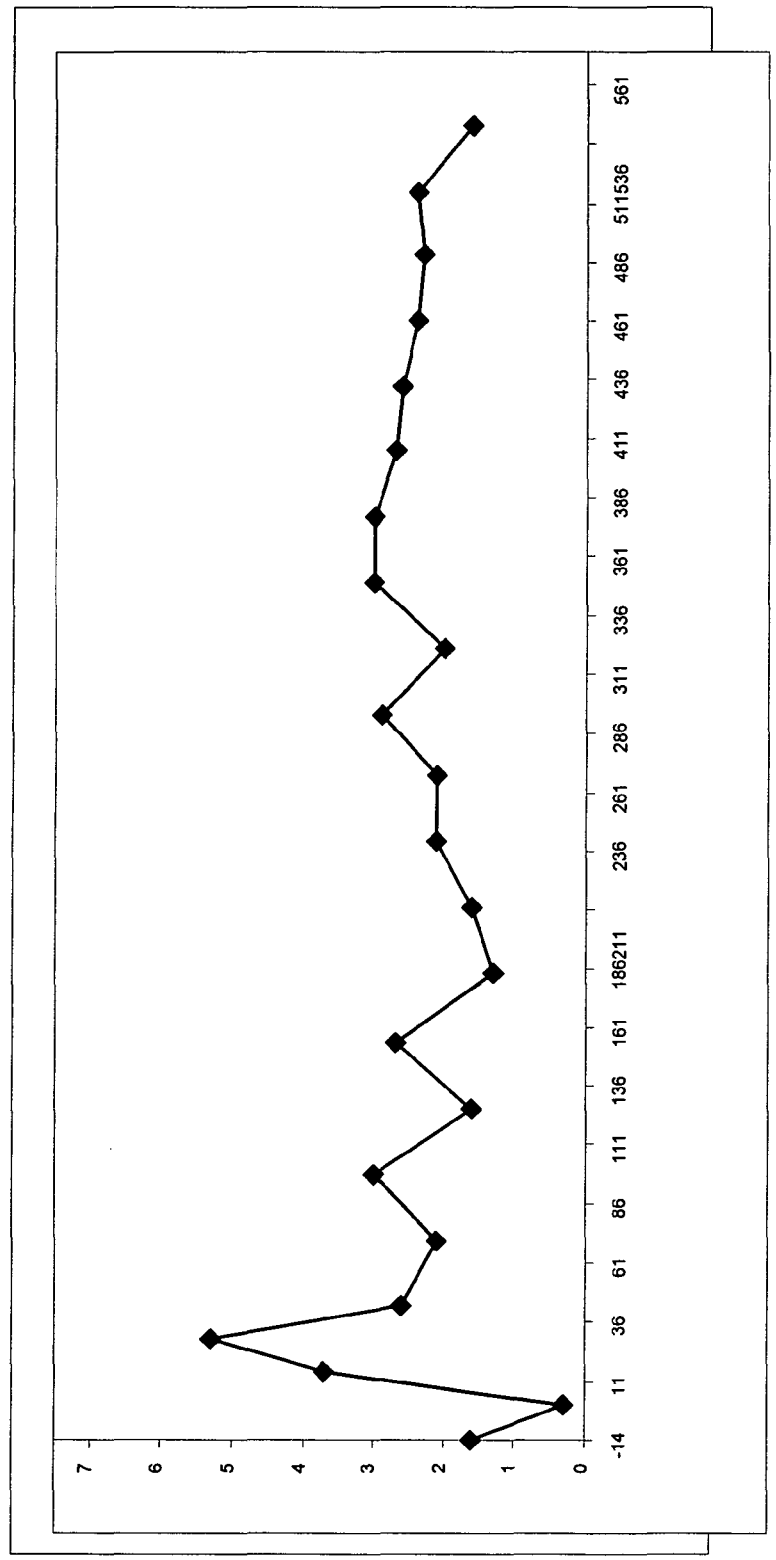

In a third aspect of the invention it was shown that the value of prostate specific antigen (PSA) can be significantly reduced in CRPC patients. The effect is dependent on the duration of the treatment and the disease status of the patient. In general after five or more months of treatment a PSA value can be obtained, which corresponds in less progressive cases to PSA values of healthy males, in other more severe cases, where the PSA value was dramatically high at the beginning of the antibody treatment, the PSA value after treatment can be reduced more than 10-fold (FIGS. 4, 5)

In a fourth aspect of the invention it could be demonstrated that by the administration of DI17E6 in a dose of at least 500 mg each two weeks the metastatic affection of bone and lymph nodes can be significantly reduced.

In a further aspect of the invention, it could be shown that DI17E6 reveals a dose-dependent response in prostate cancer patients, preferably castrate-resistant prostate cancer (CRPC) patients, with increasing efficacy at higher doses, wherein a dose of about 500 mg and higher each two weeks is effective, whereas a dose of about 250 mg DI17E6 or less is not effective in prostate cancer, preferably CRPC patients (FIG. 3, 5).

It should be noted that DI17E6 is effective preferably in a monotherapy setting, wherein no further cytotoxic drug (such as cabazitaxel, docetaxel, doxorubicin, irinotecan etc.) was administered. This is the first time, where an engineered monoclonal antibody is effective in a tumor therapeutic approach without the necessity of the administration of a chemotherapeutic agent.

It should be further noted that according to the first results in said clinical trials DI17E6 seems to be the more effective the more progressive the disease is. Thus, DI17E6 elicits a stronger effect on PSA values, circulating tumor cells and metastases in patients after ineffective hormone- and/or chemotherapy and even after surgery impacts such as prostatectomy as compared to patients in a less progressive disease state without such surgery or even without pretreatment with chemotherapeutics and/or hormones. In summary, DI17E6 is very promising in the treatment of CRPC above all in patients with a progressive or end-stage disease status after chemotherapy treatment.

A further result is that DI17E6 is able to induce tumor shrinkage and tumor lesion (FIG. 6), especially in solid prostate tumors or tumor metastases deriving thereof, which are resistant to chemotherapy and/or radiotherapy.

Furthermore, there is evidence that treatment with DI17E6 (in monotherapy) reduces pain, which usually occurs in prostate cancer. Thus, the drug presents benefits in terms of pain and pain interference score (FIGS. 4B, 5B). It could be observed that the decrease of pain during treatment is correlated with the decreasing PSA level in said patients.

DI17E6 is well tolerated without premedication, and does not show clinically relevant does-related changes in assessed safety parameters, such as drug-related treatment emergent adverse events (TEAE) (Table 3).

Figure 7:
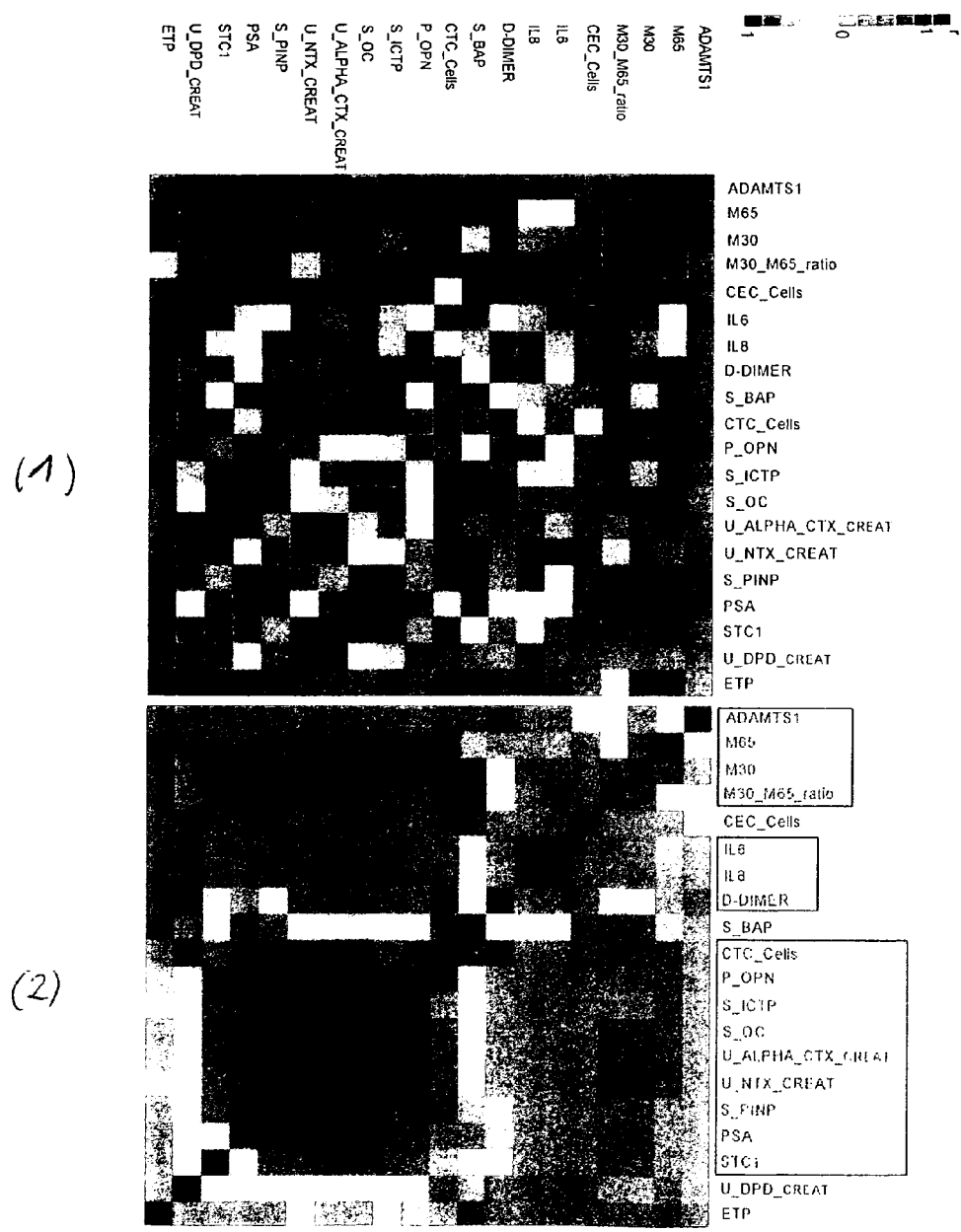

In a further aspect of the invention, it could be shown that there is a strong correlation between bone metabolism biomarkers, including STC-1, ADAMTS-1, M30, M65, IL6 and IL8, and dose levels (FIG. 7). At high doses>1500 mg a significant drop in osteopontin can be observed in the majority of CRCP patients.

The pharmacokinetic profile of DI17E6 is dependent on dose after single and multiple doses with a half-life of approximately 250 h at the 1500 mg dose level.

The safety results of the phase 1, open-label study show that repeated infusions of single-agent DI17E6 (EMD 525797) at each of four dose levels are generally well tolerated and appear to be safe in patients with mCRPC and progressive disease preferably following prior chemotherapy. There are no dose-limiting toxicities (DLT) and no infusion reactions. With regard to dose, no trends in the distribution of TEAEs, NCI-CTCAE (version 3.0) grade or drug relationship are observed. In addition, there is no evidence of accumulation of any specific event within individual cohorts. Eleven patients experienced TEAEs that are considered to be drug-related. In this regard, skin symptoms such as pruritus, erythema and rash, which are reported in a total of four patients, are predictable adverse events associated with DI17E6 (EMD 525797) given that integrins are responsible for the maintenance of the epithelial phenotype. Symptoms of mucosal inflammation and swollen tongue may also be characteristic of the mechanism of action of EMD 525797, but together with fatigue, might also be signs of the underlying disease. The hematologic and biochemic toxicity shifts observed in eight patients could also be explained by underlying disease, as well as concomitant medications.

PK assessment after single and multiple doses of study drug suggest that DI17E6 (EMD 525797) behaved in accordance with a receptor-mediated clearance model as described for other antibodies targeting membrane-associated receptors. Consistent with the findings of an earlier study in healthy volunteers, PKs of DI17E6 (EMD 525797) in mCRPC patients are dose-dependent with clearance determined predominantly by the availability of unbound receptors. At the doses used in the present study, it can be assumed that at doses of 1000 mg or higher, almost all receptors are saturated and have a minor contribution to drug clearance. Immunologically triggered antibodies directed against DI17E6 can be detected in some (16%) patients; however, no impact on PKs or safety could be found.

In castrate-resistant prostate cancer patients with bone metastases following prior chemotherapy, the median progression free survival is expected to be 8 to 10 weeks. Antitumor activity evaluations showed that DI17E6 (EMD 525797), as single-agent therapy, achieved an objective partial tumor response in a single patient in the 500 mg cohort. In 9 of 18 patients (50%) receiving DI17E6 (EMD 525797) at a dose of 500 mg or higher, no radiographic disease progression can be observed for 16 weeks or longer. In two patients, long-term treatment with DI17E6 (EMD 525797) at a dose of 500 mg is associated with significant reductions in PSA levels and clinical benefit in terms of pain interference. At least one patient also showed primary tumor shrinkage and normalization of target lymph node size. Thus, DI17E6 (EMD 525797) appears to show single-agent activity in at least some patients with late-stage mCRPC.

In conclusion, single-agent EMD 525797 given as single and multiple doses is shown to be well tolerated in patients with mCRPC with bone metastases and progressive disease following prior chemotherapy with no spontaneous remissions. No safety concern can be identified and there is preliminary evidence of clinical benefit in numerous patients. Due to its target and safety profile, DI17E6 (EMD 525797) is a promising agent for combination therapy.

To sum up, the subject matter of this invention is directed to the following:

The use of anti-av integrin antibody DI17E6 or a biologically active variant, or modification thereof, for the treatment of patients, or for the manufacture of a medicament for the treatment of patients, said patients suffering from prostate cancer, preferably castrate-resistant prostate cancer (CRPC), preferably wherein said CRPC is accompanied by high levels of serum PSA in a range of 25-10.000 ng/ml, more specifically in levels of more than 25 ng/ml, or more than 50 ng/ml, or more than 100 ng/ml, or more than 250 mg/ml, or more than 500 ng/ml, or more than 1000 ng/ml, or more than 2500 ng/ml or more than 5000 ng/ml, or more than 7500 ng/ml.

The respective use of DI17E6 antibody, wherein the cancer is metastasizing, preferably into bone and/or lymph node tissue.

The respective use of DI17E6 antibody, wherein the prostate-specific antigen (PSA) value is declined more than 5-fold, 10-fold, 20-fold, preferably 10-fold during treatment compared to the value before starting antibody treatment.

The respective use of DI17E6 antibody, wherein the reduction of the PSA value was achieved within 4-8 months of treatment, preferably after 4 months, more preferably after 6 months.

The respective use of DI17E6 antibody, wherein the number of the circulating tumor cells (CTC) is declined during antibody treatment.

The respective use of DI17E6 antibody in a CRPC patient whose prostate has been removed, or alternatively, has been treated by radiation.

The respective use of DI17E6 antibody for reducing pain which occurs in prostate cancer, preferably in CRPC preferably accompanied by bone metastasis.

The respective use of DI17E6 antibody, wherein the patient was pretreated with chemotherapeutics and/or hormonal agents, preferably when the cancer is progressive after said pretreatment with the chemotherapeutic and/or hormonal agent.

The respective use of DI17E6 antibody, wherein the effective dose of the antibody is 500 mg-1500 mg per two weeks, preferably 500-1000 mg per two weeks, or 1000-2000 mg per month.

The respective use of DI17E6 antibody, wherein the effective dose of 500-1000 mg is administered by a single infusion.

The respective use of DI17E6 antibody, wherein the antibody is administered in a monotherapy setting without additional chemotherapeutic agents.

The respective use of DI17E6 antibody, wherein the antibody is administered in a combinatory setting with a cytotoxic/cytostatic or an hormonal agent sequentially or simultaneously.

The respective use of DI17E6 antibody, wherein in said combinatory setting the cytostatic or cxytotoxic agent is selected from the group consisting of: a chemotherapeutic agent, radiation, a tyrosine kinase inhibitor, and an angiogenesis inhibitor; said tyrosine kinase inhibitor being an anti-ErbB antibody selected from the group consisting of an anti-EGFR antibody, an anti-Her2 antibody, and an anti-Her3 antibody, and said angiogenesis inhibitor being an alpha-v integrin inhibitor, preferably an RGD peptide, such as cilengitide.

The respective use of DI17E6 antibody, wherein the biologically active variant or modification comprises the CDR regions and heavy and light chain variable regions, which are 80%-95% identical in amino acid sequence compared to the variable regions of DI17E6.

The respective use of DI17E6 antibody, wherein the biological active variant or modification comprises a constant region, which is at least 80%-98% identical with the amino acid sequence compared to the constant region of DI17E6.

The respective use of DI17E6 antibody, comprising one or more modifications within the heavy chain framework regions FR1: QVQLQQSGAELAEPGASVKMSCKASGYTFS (SEQ ID No. 16)

FR2: WVKQRPGQGLEWIG (SEQ ID No. 17)

FR3: KATMTADTSSSTAYMQLSGLTSEDSAVYYCAS (SEQ ID No. 18)

FR4: WGQGTSVTVSS, (SEQ ID No. 19)

wherein one or more of the bold and underlined positions are mutated and are different compared to the original respective sequence.

The respective use of a modified DI17E6 antibody comprising a human IgG1 constant region instead of human IgG2, or a human IgG2 hinge region instead of the human IgG1 hinge.

A method of treating castrate-resistant prostate cancer (CRPC) in a patient, preferably accompanied by bone metastases, comprising administering the anti-av integrin antibody DI17E6 or a biologically active variant, or modification thereof preferably in a dose of 500-1000 mg each two weeks preferably for a period of at least three months.

A method of declining the pathologically increased PSA serum level of a patient suffering from prostate cancer, preferably castrate-resistant prostate cancer (CRPC) more than 5-fold, preferably more than 10-fold by administering to said patient the hybrid monoclonal antibody DI17 in an effective dose of at least 500 mg each two weeks, or at least 1000 mg per month, wherein the pathological increased PSA serum level before staring antibody treatment is at least 25 ng/ml, preferably at least 50 ng/ml.

A respective method, wherein the cancer is metastasizing in bone and/or lymph node tissue.

SHORT DESCRIPTION OF THE FIGURES

FIG. 1: shows a table summarizing the results of the measuring of circulating tumor cells (CTC) in six selected CRPC patients of dose level (1) 250 mg, (2) 500 mg, and (3) 1000 mg. X-axis indicates days of treatment. Y-axis indicates circulating tumor cells (CTC).

Figure 2:
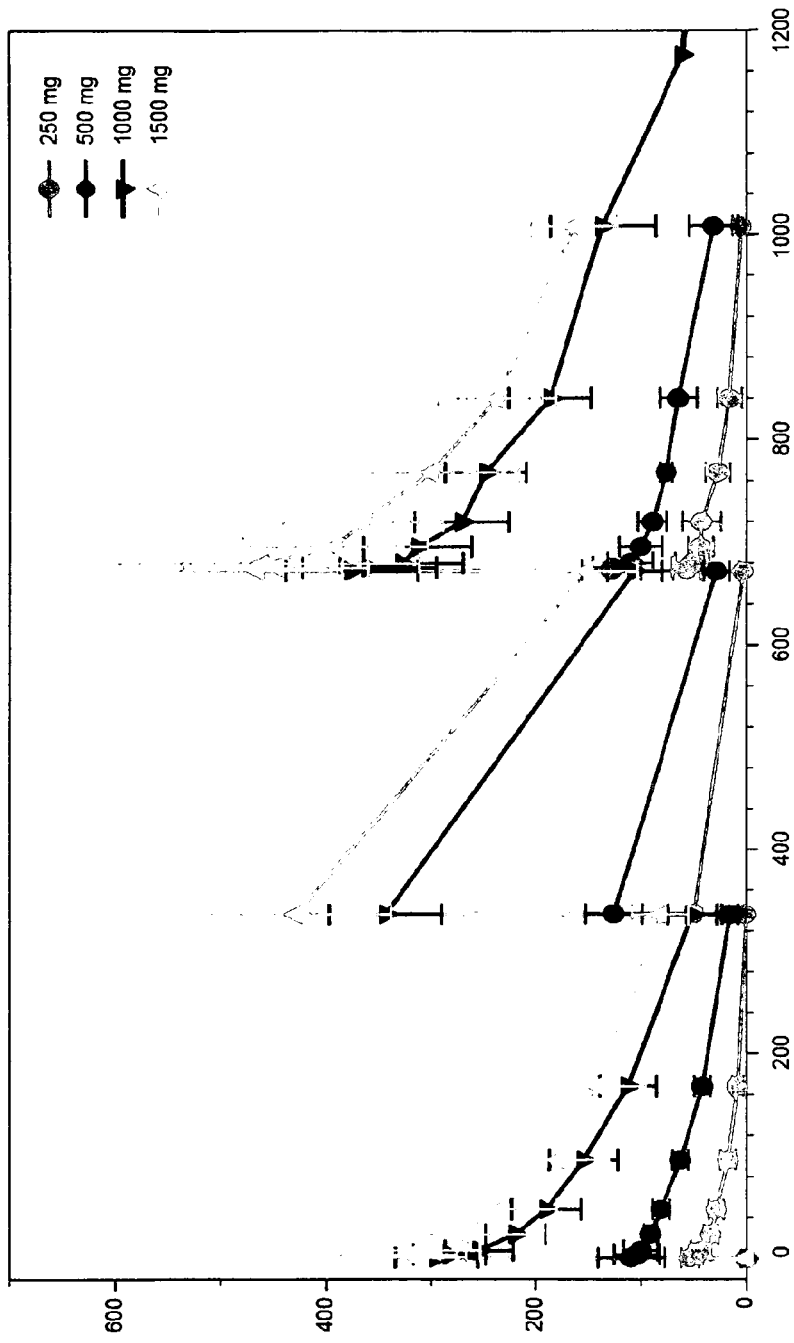

FIG. 2: shows dose-depend pharmacokinetic profile of DI17E6 (EMD 525797) for 250 mg, 500 mg, 1000 mg and 1500 mg Ab administered per each 4 weeks. X-axis indicates time after first infusion (h); Y-axis indicates serum concentration (µg/ml).

FIG. 3: shows the treatment duration of a cohort of CRPC patients after the treatment with DI17E6; X-axis: number of weeks treatment; Y-axis: Dose levels (dose level 1: 250 mg, dose level 2: 500 mg, dose level 3: 1000 mg, dose level 4: 1500 mg)

FIG. 4: (A) shows the change of the PSA level (ng/ml serum) in a specific CRPC patient (2001) without prostatectomy showing bone metastases during the treatment with DI17E6 (treatment start 24 Aug. 2009). (A). X-axis indicates the duration of treatment (days); Y-axis indicates PSA level (ng/ml) (B) shows the average pain interference score as defined below of the same patient of (A). X-axis indicates the duration of treatment (days); Y-axis indicates average pain interference score.

FIG. 5: (A) shows the PSA course of a second CRPC patient with progressive disease after chemotherapy showing bone metastases and prostatectomy during the treatment with DI17E6 (treatment start 1 Sep. 2009). (A). X-axis indicates the duration of treatment (days); Y-axis indicates PSA level (ng/ml) (B) shows the average pain interference score as defined below of the same patient of (A). X-axis indicates the duration of treatment (days); Y-axis indicates average pain interference score.

Figure 6:
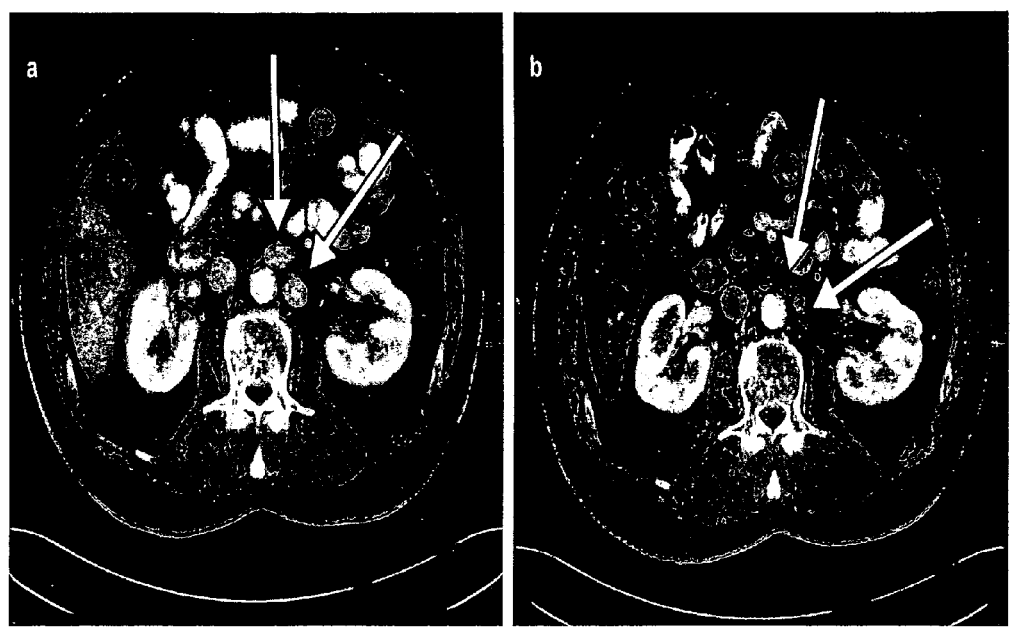

FIG. 6: shows a CT scan of a patient from the 500 mg cohort showing significant shrinkage of primary tumor lesions: (a) before treatment with DI-17E6, (b) after the 17th treatment with DI-17E6 (after 4 months).

FIG. 7: shows the occurrence of bone markers/circulating bone markers after the treatment with DI17E6. 1=dose level 1; 2=dose level 2

DETAILED DESCRIPTION OF THE INVENTION

DI17E6 is an engineered specifically tailored IgG2 hybrid monoclonal antibody directed to alpha-v integrin (receptor). Cancer therapy by means of this antibody reduces side effects associated with this type of therapy, above all immune reactions, thereby reducing immunogenicity. The antibody is described in detail in WO 2009/010290.

Its hypervariable regions (CDRs) derive from murine mAb 17E6 (EMD 73034). This parent mouse IgG1 antibody is described, for example by Mitjans et al. (1995; J. Cell Sci. 108, 2825) and U.S. Pat. No. 5,985,278 and EP 719 859. Mouse mAb 17E6 is produced by hybridoma cell line 272-17E6 and deposited under accession number DSM ACC2160.

Its light chain domains derive from humanized monoclonal anti-EGFR antibody 425 (matuzumab). This antibody is described in detail for example in EP 0 531 472B1, and derives from its murine counterpart 425 (mouse MAb 425, ATCC HB9629), The antibody was raised against the human A431 carcinoma cell line and found to bind to a polypeptide epitope on the external domain of the human epidermal growth factor receptor (EGFR). Matuzumab has shown in clinical trials high efficacy.

Generally DI17E6 as used according to the invention comprises:
(i) a CDR light and a heavy chain region deriving from mouse monoclonal anti-αv integrin antibody 17E6
(ii) a light chain framework region which is taken from humanized monoclonal anti-EGFR antibody 425,
(iii) a heavy chain framework region deriving from mouse monoclonal anti-αv integrin antibody 17E6, optionally comprising one or more mutations of amino acids at specific positions, and
(iv) a heavy chain constant region deriving from human IgG2 and a human constant kappa light chain region, wherein in said IgG2 domain the IgG2 hinge region was replaced by the human IgG1 hinge domain, and; wherein optionally one or more mutations within the IgG2 has been carried out.

Specifically, DI17E6 (designated as "DI-17E6γ2h (N297Q)" or "EMD 525797") as used for the treatment as claimed and in the clinical trials as described above and below, has the following amino acid sequence:

```
(i) variable and constant
light chain sequences (SEQ ID No. 1):
DIQMTQSPSSLSASVGDRVTITCRASQDISNYLAWYQQKPGKAPKLLIYY

TSKIHSGVPSRFSGSGSGTDYTFTISSLQPEDIATYYCQQGNTFPYTFGQ
```

```
GTKVEIKRTVAAPSVFIFPPSDEQLKSGTASVVCLLNNFYPREAKVQWKV

DNALQSGNSQESVTEQDSKDSTYSLSSTLTLSKADYEKHKVYACEVTHQG

LSSPVTKSFNRGEC
and (ii) variable and constant
heavy chain sequences (SEQ ID No. 2):
QVQLQQSGGELAKPGASVKVSCKASGYTFSSFWMHWVRQAPGQGLEWIGY

INPRSGYTEYNEIFRDKATMTTDTSTSTAYMELSSLRSEDTAVYYCASFL

GRGAMDYWGQGTTVTVSSASTKGPSVFPLAPCSRSTSESTAALGCLVKDY

FPEPVTVSWNSGALTSGVHTFPAVLQSSGLYSLSSVVTVPSSNFGTQTYT

CNVDHKPSNTKVDKTVEPKSSDKTHTCPPCPAPPVAGPSVFLFPPKPKDT

LMISRTPEVTCVVVDVSHEDPEVQFNWYVDGVEVHNAKTKPREEQAQSTF

RVVSVLTVVHQDWLNGKEYKCKVSNKGLPAPIEKTISKTKGQPREPQVYT

LPPSREEMTKNQVSLTCLVKGFYPSDIAVEWESNGQPENNYKTTPPMLDS

DGSFFLYSKLTVDKSRWQQGNVFSCSVMHEALHNHYTQKSLSLSPGK,
``` wherein the underlined sequences represent the variable regions with the CDRs (in bold, identical with the parent mouse antibody). The modified IgG1 hinge region is represented by EPKSSDKTHTCPPCP (SEQ ID No. 3), and AQ is a substitution within the IgG2 domain.

However, as it was shown in WO 2009/010290, also variants of DI17E6 can be used according to the teaching of this invention. Thus, DI17E6 variants comprising one or more modifications within the heavy chain framework regions

```
                                        (SEQ ID No. )
FR1:  QVQLQQSGAELAEPGASVKMSCKASGYTFS (SEQ ID No. 17)
FR2:  WVKQRPGQGLEWIG (SEQ ID No. )
FR3:  KATMTADTSSSTAYMQLSGLTSEDSAVYYCAS (SEQ ID No. 19)
FR4:  WGQGTSVTVSS,
``` wherein one or more of the bold and underlined positions are mutated, can be used in the treatment of prostate cancer patients as described. In more detail, the following position heavy chain framework region is mutated at one, more or all of the following positions can be mutated: A9, E13, M20, K38, R40, A72, S76, Q82, G85, T87, S91 and S113. These variants show the same or very similar biological activity and efficacy as compared to DI17E6 defined by its sequences above.

In general, the invention as described includes also modifications and variants of the DI17E6 antibody that are functionally and/or pharmaceutically identical or similar to unmodified DI17E6, and wherein the CDR regions and heavy and light chain variable regions are at least 80%, or at least 85%, or at least 90%, or at least 95% identical in their amino acid sequence compared to the respective variable regions of DI17E6. In addition, the invention also includes modifications and variants of the DI17E6 antibody that are functionally and/or pharmaceutically identical or similar to unmodified DI17E6, and wherein the constant regions are at least 80%, or at least 85%, or at least 90%, or at least 98% identical in their amino acid sequence compared to the respective constant regions of DI17E6. Changes is the constant regions of the IgG chains of the antibody may improve specific properties like immunogenicity, ADCC, and so on.

In a further aspect, the DI17E6 antibody as used according to the invention can be fused to a cytotoxic agent, preferably a cytokine, such as IL2, IL8, IFNb, IFNa, TNFa, GM-CSF, G-CSF, or as specified below. The cytokine can be fuses via its N-terminal to the C-terminal of the antibody heavy chains, or via its C-terminal to the N-terminal of the heavy and light chain of the antibody.

According to the invention, DI17E6 is highly effective in patients suffering from prostate cancer, above all in patients whose tumor is progressive after chemotherapy and/or hormonal therapy and/or prostate surgery such as prostatectomy.

In order to strengthen or prolong efficacy of DI17E6 or its modifications described a combination therapy together with cytotoxic or cytostatic agents is applicable. The cytostatic or cytotoxic agent can be administered in sequential steps with the antibody or simultaneously in doses that are quite common and convenient in the clinical treatment of cancer. Preferred cytotoxic/cytostatic agents according to the invention are anti-angiogenic agents as described below in more detail, anti-EGFR or -Her3 agents including respective antibodies, such as Herceptin® (trastuzumab), Erbitux® (cetuximab) or panitumumab. In a preferred embodiment the combination therapy of DI17E6 together with cetuximab is effective in prostate cancer, especially in CRPC according to this invention.

For the same purpose DI17E6 can be administered together (sequentially or simultaneously) with hormonal agents according to known regimen.

The term "castrate-resistant" or "castration-resistant" as used herein refers to a status in prostate cancer wherein the disease is progressing with serum testosterone controlled below a castrate level, which is usually <50 ng/100 ml. The term is synonymously used with "hormone-resistant" or "hormone-refractory" or "androgen-independent".

The term "pain interference (total) score" means a score for pain as a result of the disease occurring during administration of the effective drug. Pain interference is assessed using the Brief Pain Inventory (BPI). BPI is used to evaluate pain interference with the following: (a) general activity, (b) mood, (c) walking ability, (d) normal work, (e) relations with other people, (f) sleep, and (g) enjoyment of life. Total score for pain interference is calculated as: (Mean score of non-missing questions)×(7/number of non-missing questions). If four or more questions are missing, the pain interference total score is set to missing.

The term "cytotoxic agent" as used herein refers to a substance that inhibits or prevents the function of cells by causing destruction of cells. The term is intended to include radioactive isotopes, chemotherapeutic agents, and toxins such as enzymatically active toxins of bacterial, fungal, plant or animal origin, or fragments thereof. The term may include also members of the cytokine family, preferably IFNγ as well as anti-neoplastic agents having also cytotoxic activity.

The term "cytostatic agent" as used herein refers to a substance that inhibits or suppresses cellular growth and multiplication without destroying cells.

The term "cytokine" is a generic term for proteins released by one cell population which act on another cell as intercellular mediators. Examples of such cytokines are lymphokines, monokines, and traditional polypeptide hormones. Included among the cytokines are growth hormone such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; fibroblast growth factor; prolactin; placental lactogen; mouse gonadotropin-associated peptide; inhibin; activin; vascular endothelial growth factor (VEGF); integrin; thrombopoietin (TPO); nerve growth factors such as NGFβ; platelet-growth factor; transforming growth factors (TGFs) such as TGFα and TGFβ; erythropoietin (EPO); interferons such as IFNα, IFNβ, and IFNγ; colony stimulating factors such as M-CSF, GM-CSF and G-CSF; interleukins such as IL-1, IL-1a, IL-2, IL-3, IL-4, IL-5, IL-6, IL-7, IL-8, IL-9, IL-10, IL-11, IL-12; and TNFα or TNFβ. Preferred cytokines according to the invention are interferons and TNFa.

An "anti-angiogenic agent" refers to a natural or synthetic compound which blocks, or interferes with to some degree, the development of blood vessels. The anti-angiogenic molecule may, for instance, be a biological molecule that binds to and blocks an angiogenic growth factor or growth factor receptor. The preferred anti-angiogenic molecule herein binds to an receptor, preferably to an integrin receptor or to VEGF receptor. The term includes according to the invention also integrin (receptor) inhibitors.

The term "integrin inhibitors" or "integrin receptor inhibitors" refers to a natural or synthetic molecule that blocks and inhibit an integrin receptor. In some cases, the term includes antagonists directed to the ligands of said integrin receptors (such as for $\alpha_v\beta_3$: vitronectin, fibrin, fibrinogen, von Willebrand's factor, thrombospondin, laminin; for $\alpha_v\beta_5$: vitronectin; for $\alpha_v\beta_1$: fibronectin and vitronectin; for $\alpha_v\beta_6$: fibronectin). Antagonists directed to the integrin receptors are preferred according to the invention. Integrin (receptor) antagonists may be natural or synthetic peptides, non-peptides, peptidomimetica, immunoglobulins, such as antibodies or functional fragments thereof, or immunoconjugates (fusion proteins). Preferred integrin inhibitors of the invention are directed to receptor of $\alpha_v$ integrins (e.g. $\alpha_v\beta_3$, $\alpha_v\beta_5$, $\alpha_v\beta_6$ and sub-classes). Preferred integrin inhibitors are $\alpha_v$ antagonists, and in particular $\alpha_v\beta_3$ antagonists. Preferred $\alpha_v$ antagonists according to the invention are RGD peptides, peptidomimetic (non-peptide) antagonists and anti-integrin receptor antibodies such as antibodies blocking $\alpha_v$ receptors. Exemplary, non-immunological $\alpha_v\beta_3$ antagonists are described in the teachings of U.S. Pat. No. 5,753,230 and U.S. Pat. No. 5,766,591. Preferred antagonists are linear and cyclic RGD-containing peptides. Cyclic peptides are, as a rule, more stable and elicit an enhanced serum half-life. The most preferred integrin antagonist of the invention is, however, cyclo-(Arg-Gly-Asp-DPhe-NMeVal) (EMD 121974, Cilengitide®, Merck KgaA, Germany; EP 0770 622) which is efficacious in blocking the integrin receptors $\alpha_v\beta_3$, $\alpha_v\beta_1$, $\alpha_v\beta_6$, $\alpha_v\beta_8$, $\alpha_{IIb}\beta_3$. A combination therapy of DI17E6 together with Cilengitide in prostate cancer and preferably CRPC patients is effective according to the invention.

The term "chemotherapeutic agent" or "anti-neoplastic agent" is regarded according to the understanding of this invention as a member of the class of "cytotoxic agents", as specified above, and includes chemical agents that exert anti-neoplastic effects, i.e., prevent the development, maturation, or spread of neoplastic cells, directly on the tumor cell, and not indirectly through mechanisms such as biological response modification. Suitable chemotherapeutic agents according to the invention are preferably natural or synthetic chemical compounds, but biological molecules, such as proteins, polypeptides etc. are not expressively excluded. There are large numbers of anti-neoplastic agents available in commercial use, in clinical evaluation and in pre-clinical development, which could be included in the present invention for treatment of tumors/neoplasia by combination therapy with TNFα and the anti-angiogenic agents as cited above. It should be pointed out that the chemotherapeutic agents can be administered optionally together with above-said antibody drug. Examples of chemotherapeutic or agents include alkylating agents, for example, nitrogen mustards, ethyleneimine compounds, alkyl sulphonates and other compounds with an alkylating action such as nitrosoureas, cisplatin and dacarbazine; antimetabolites, for example, folic acid, purine or pyrimidine antagonists; mitotic inhibitors, for example, vinca alkaloids and derivatives of podophyllotoxin; cytotoxic antibiotics and camptothecin derivatives. Preferred chemotherapeutic agents or chemotherapy include amifostine (ethyol), cabazitaxel, cisplatin, dacarbazine (DTIC), dactinomycin, docetaxel, mechlorethamine, streptozocin, cyclophosphamide, carrnustine (BCNU), lomustine (CCNU), doxorubicin (adriamycin), doxorubicin lipo (doxil), gemcitabine (gemzar), daunorubicin, daunorubicin lipo (daunoxome), procarbazine, ketokonazole, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil and combinations thereof. Most preferred chemotherapeutic agents according to the invention in combination with DI17E6 are cabazitaxel, cisplatin, docetaxel, gemcitabine, doxorubicin, paclitaxel (taxol), irinotecan and bleomycin.

DI17E6 is administered usually by intravenous injection, however other administration forms convenient in the art for antibody/protein drugs are applicable. All standard infusion solutions and formulation are applicable, such as described in WO 2005/077414 or WO 2003/053465, including liposomal formulations. It is, in addition, favorable to provide human serum albumin nanoparticles loaded with DI17E6 and optionally (to increase cytotoxicity) chemotherapeutic drugs (Biomaterials 2010, 8, 2388-98; Wagner et al.).

The following examples describe the invention in more details but do not limit the invention and its scope as claimed.

EXAMPLES

Example 1

Study Design

A Phase I trial was initiated to determine safety, pharmacokinetics, and antitumor activity of CRPC patients treated with DI17E6 including effects on prostate-specific antigen, circulating tumor cells (CTC), and soft tissue and bone metastases. All patients were suffering from a progressing disease after chemotherapy. Patients were treated with iv-infusions of 250, 500, 1000 or 1500 mg DI17E6 given over 1 hour.

Eligible patients were aged 18 years or older and had histologically or cytologically proven prostate cancer with evidence of bone metastases after prior chemotherapy. Patients had either undergone bilateral orchidectomy or were receiving continuous androgen deprivation therapy with a gonadotropin releasing hormone agonist or antagonist and had stopped anti-androgen therapy for at least 4 weeks prior to enrolment. Patients were required to either be on stable (i.e. at least 3 months) ongoing bisphosphonate therapy or without any bisphosphonate therapy, with a total serum testosterone level less than 50 ng/dL. All patients had evidence of progressive disease, defined as at least two prostate-specific antigen (PSA) values above the individual nadir level with a minimum increase of 10% each determined at least two weeks prior to screening; nodal or visceral progression was sufficient for inclusion independent of PSA. In addition, patients had to have an Eastern Cooperative Oncology Group (ECOG) score of 0 to 2, a life expectancy of at least 3 months, and adequate hematologic, renal and hepatic function. An institutional review board at each study center approved the study protocol, and all patients provided written informed consent.

In this phase 1, multicenter, open-label, dose-escalation study, mCRPC patients were administered three intravenous infusions of EMD 525797 at doses of 250, 500, 1000, or 1500 mg given over one hour every two weeks prior to response assessment at the end of week 6. Patients without evidence of progressive disease were eligible to receive further fortnightly doses until disease progression or unacceptable toxicity. Dose-limiting toxicities (DLTs) were assessed during the first six weeks and patients were followed for safety until four weeks after the last administration of EMD 525797. Patients were recruited in four sequential dose cohorts; after the last of six patients within a dose cohort had reached the end of week 6, a Safety Monitoring Committee determined subsequent dose escalation.

Twenty-six male patients aged between 43 and 80 years (median age, 66 years) were enrolled and received at least one intravenous infusion of EMD 525797, constituting the safety population. All patients were of Caucasian origin. In general, demographic characteristics were comparable across the four dose cohorts (Table 1a), with a median time since first diagnosis of 5.2 years (range, 2-18 years) and a median time from diagnosis to first metastatic disease of 0.1 years (range, 0-16 years). Two patients withdrew before the end of the DLT period and were subsequently replaced, with 24 patients receiving three doses of EMD 525797 through treatment Week 6.

TABLE 1a

Patient baseline demographics (safety population).

| | DI17E6 (EMD 525797) dose cohort | | | | |
| --- | --- | --- | --- | --- | --- |
| Characteristic | 250 mg (N = 8) | 500 mg (N = 6) | 1000 mg (N = 6) | 1500 mg (N = 6) | Total (N = 26) |
| Age, years, mean (range) | 67 (57-78) | 63 (47-77) | 62 (43-79) | 66 (52-80) | 65 (43-80) |
| Weight, kg, mean | 82.2 | 85.8 | 80.5 | 93.7 | 85.3 |

TABLE 1a-continued

Patient baseline demographics (safety population).

| | DI17E6 (EMD 525797) dose cohort | | | | |
|---|---|---|---|---|---|
| Characteristic | 250 mg (N = 8) | 500 mg (N = 6) | 1000 mg (N = 6) | 1500 mg (N = 6) | Total (N = 26) |
| BMI, kg/m², mean | 26.2 | 28.1 | 26.0 | 28.9 | 27.2 |
| TNM stage* at diagnosis, n (%) | | | | | |
| II | 1 (12.5) | 3 (50.0) | 0 | 1 (16.7) | 5 (19.2) |
| III | 2 (25.0) | 1 (16.7) | 0 | 1 (16.7) | 4 (15.4) |
| IV | 5 (62.5) | 2 (33.3) | 5 (83.3) | 2 (33.3) | 14 (53.8) |
| Missing | 0 | 0 | 1 (16.7) | 2 (33.3) | 3 (11.5) |
| Previous anticancer therapy, n (%) | | | | | |
| Hormonal therapy | 8 (100) | 6 (100) | 5 (83.3) | 6 (100) | 25 (96.2) |
| Immunotherapy | 1 (12.5) | 0 | 0 | 0 | 1 (3.8) |
| Radiotherapy | 7 (87.5) | 3 (50.0) | 3 (50.0) | 4 (66.7) | 17 (65.4) |
| Chemotherapy | 8 (100) | 6 (100) | 6 (100) | 6 (100) | 26 (100) |
| Surgery | 6 (75) | 2 (33.3) | 3 (50.0) | 2 (33.3) | 13 (50.0) |

BMI, body mass index;
TNM, tumor, node, metastasis.

In summary (Table 1b):

| | |
|---|---|
| Objectives | Safety, tolerability and PK after multiple rising i.v. doses<br>Determine changes in markers of bone metabolism during treatment<br>Investigate changes in efficacy parameters within the whole dose range<br>Identification of potential pharmacodynamic markers |
| Subject population | Subjects with prostate cancer with evidence of bone metastases after prior chemotherapy with e.g. taxane or mitoxantrone |
| Number of subjects | Per dose level n = 6 |
| Dose selection | 250, 500, 1000, 1500 mg as 1 h i.v. infusion |
| Treatment duration | 6 weeks (every second week) and 4 weeks follow up.<br>Option for further treatment if patient is non-progressive. |
| Dose escalation | Dose escalation will be based on the toxicity assessment (DLT) after 6 weeks. |

The clinical results from this Phase I clinical trial is being conducted at 3 sites in Germany and at one site in Belgium and show single agent and biological activity in subjects with castration-resistant prostate cancer with bone metastases and progressive disease after chemotherapy.

Example 2

Treatment Duration 24 patients (43-80 years) received 3 doses (weeks 1, 3 and 5) prior to response assessment at the end of week 6. Patients without progressive disease could receive further doses every 2 weeks. Dose-limiting toxicities (DLTs) were assessed over the first 6 weeks and patients were followed for safety until 4 weeks after the last administration of DI17E6.

Table 2 summarizes drug exposure per patient in each cohort. Patients had a mean EMD 525797 exposure duration of 117.5 days (median, 74.5 days; range, 14-534 days). Thirteen of 24 patients had a longer exposure time than expected (>84 days), with two patients in the 500 mg cohort remaining on treatment for 297 and 534 days, and one patient in the 1000 mg cohort receiving treatment for 310 days. No DLTs were reported within the DLT period of 6 weeks. All patients experienced at least one TEAE and no dose-dependent relationship in TEAEs was observed.

TABLE 2a

DI17E6 exposure per patient in each of the dose cohorts

| Pt | 250 mg | 500 mg | 1000 mg | 1500 mg |
|---|---|---|---|---|
| 1 | 42 | 297 | 113 | 91 |
| 2 | 42 | 380+ | 121 | 84+ |
| 3 | 42 | 85 | 198+ | 72+ |
| 4 | 42 | 142 | 41 | 64+ |
| 5 | 56 | 140 | 56 | 77+ |
| 6 | 98 | 56 | 43 | 57+ |
| 7 | 14* | | | |
| 8 | 28* | | | |

+= ongoing treatment;
*dropped out pts (1 and 2 infusions only)

The study protocol stated, that subjects will receive every other week at least 3 doses (250, 500, 1000 mg/each 2 weeks) of DI17E6 and that subjects without evidence of progressive disease will receive further treatment doses every other week.

Treatment duration in all 4 cohorts (state: August 2010). Cohort 2 with 500 mg/each 2 weeks, two patients (2001 and 2002) in late stage (estimated mOS<12 months) are more than 10 months with unexpected tumor response on treatment.

TABLE 2b

This table shows the values of the treatment duration (state: August 2010). Dose level 1: 250 mg DI17E6; dose level 2: 500 mg DI17E6; dose level 3: 1000 mg DI17E6, and dose level 4: 1500 mg DI17E6.

| Dose Level | Patients/No. weeks treatment | | | | | | | | | | | | | |
|---|---|---|---|---|---|---|---|---|---|---|---|---|---|---|
| | 1001 | 1002 | 1003 | 1004 | 1005 | 1005 | 1006 | 1010 | 2001 | 2002 | 2003 | 2005 | 2007 | 2009 |
| 1 | 6.3 | 6.3 | 3.3 | 6.0 | 6.1 | 9.1 | 4.1 | 13.0 | | | | | | |
| 2 | | | | | | | | | 42.3 | 49.3 | 12.1 | 18.3 | 20.0 | 6.4 |
| 3 | | | | | | | | | | | | | | |
| 4 | | | | | | | | | | | | | | |

| Dose Level | Patients/No. weeks treatment | | | | | | | | | | | |
|---|---|---|---|---|---|---|---|---|---|---|---|---|
| | 3001 | 3002 | 3003 | 3004 | 3005 | 3006 | 4002 | 4003 | 4004 | 4006 | 4009 | 4011 |
| 1 | | | | | | | | | | | | |
| 2 | | | | | | | | | | | | |
| 3 | 14.1 | 17.5 | 24.3 | 6.0 | 7.1 | 6.1 | | | | | | |
| 4 | | | | | | | 9.4 | 6.4 | 8.3 | 9.1 | 8.1 | 2.43 |

Example 3

Safety/Side Effects

Table 3 summarizes drug-related TEAEs. Eleven patients (42.3%) experienced drug-related TEAEs, which were most commonly reported in the system organ class "Skin and subcutaneous tissue disorders" (4 patients total; pruritus generalized, erythema, rash), "General disorders and administration site conditions" (3 patients total; fatigue, mucosal inflammation, edema peripheral), "Gastrointestinal disorders" (2 patients total; dry mouth, swollen tongue, upper gastrointestinal hemorrhage), and "Infections and infestations" (2 patients total; rhinitis, septicemia). Only two patients (7.7%) had a drug-related grade 3 or 4 TEAE: one patient in the 500 mg cohort experienced a grade 3 increase of gamma-glutamyltransferase (GGT) and a single patient in the 1000 mg cohort experienced a grade 3 septicemia.

Two patients experienced serious TEAEs that were considered to be related to treatment. These were a grade 1 upper gastrointestinal hemorrhage in a patient in the 250 mg cohort and a grade 3 septicemia in one patient in the 1000 mg cohort. At screening, this latter patient had an ongoing diagnosis of urinary tract infection and recurrent events of septicemia of which the last event was considered related to DI17E6 (EMD 525797). Four patients died and investigators assessed all deaths as not reasonably related to EMD 525797.

Six patients (23.1%) permanently discontinued treatment due to TEAEs, including 4 patients in the 250 mg cohort (upper gastrointestinal hemorrhage at day 12, muscular weakness at day 53, paraplegia at day 46, and ureteric obstruction at day 30), and 1 patient each in the 500 mg (grade 3 GGT increase at day 534) and 1500 mg (metastases to central nervous system at day 85) cohorts. No administration site skin reactions were reported. Post-baseline hematology and biochemistry toxicity shifts to grade 3 or 4 occurred in 8 patients. However, there were no obvious trends in laboratory findings, vital signs or ECG recordings. Overall, 65.4% of patients had the same worst ECOG performance status on treatment compared with baseline.

TABLE 3

Drug-related treatment emergent adverse events* (TEAEs).

| TEAEs related to EMD 525797 | n (%) |
|---|---|
| Patients with events | 11 (42) |
| Skin and subcutaneous tissue disorders | 4 (15) |
| Pruritus generalized | 2 (8) |
| Erythema | 1 (4) |
| Rash | 1 (4) |
| General disorders and administration site conditions | 3 (12) |
| Fatigue | 1 (4) |
| Mucosal inflammation | 1 (4) |
| Edema peripheral | 1 (4) |
| Gastrointestinal disorders | 2 (8) |
| Dry mouth | 1 (4) |
| Swollen tongue | 1 (4) |
| Upper gastrointestinal hemorrhage | 1 (4) |
| Infections and infestations | 2 (8) |
| Rhinitis | 1 (4) |
| Septicemia† | 1 (4) |
| Eye disorders | 1 (4) |
| Vision blurred | 1 (4) |
| Investigations | 1 (4) |
| Blood pressure increase | 1 (4) |
| Musculoskeletal and connective tissue disorders | 1 (4) |
| Arthralgia | 1 (4) |
| Nervous system disorders | 1 (4) |
| Dysgeusia | 1 (4) |
| Respiratory, thoracic, and mediastinal disorders | 1 (4) |
| Dyspnea | 1 (4) |

*MedDRA Primary System Organ Class. MedDRA Preffered Term Version 13.0.
†Grade 3 occurred after the first 6 weeks (dose limiting toxicity period).

Examples of Observed Side Effect:

(i) A 62 year-old male experienced grade 1 upper gastrointestinal bleeding 13 days after the first and only infusion of DI17E6 (250 mg). The subject presented with non-serious hematemesis and was hospitalized. Gastroscopy showed a lesion in the distal esophagus. Active bleeding was excluded, the subject was treated with omeprazole, and the event resolved (ii) A 79 year-old patient developed septicemia (grade 2) due to e. faecalis 1 days after the most recent and 9 weeks after the first infusion of DI17E6 (EMD 525797) (1000 mg). The patient was hospitalized and discharged with recovery. A month later, the patient developed a second septicemia episode (grade3) again due to e. faecalis 4 days after the most recent and 2,5 months after the first infusion. The patient was hospitalized and discharged with recovery. Another month later, the patient developed a third septicemia episode (grade3) 4 days after the most recent and 3,5 months after the first infusion, which was attributed to EMD 525797.

In Summary:
- Accumulating safety data have been reviewed at all 4 SMCs
- Overall no DLTs have been observed: DLT is defined as any grade 3 or 4 hematological or non-hematological toxicity occurring until end of week 6 suspected to be reasonably related to the investigational product by the Investigator and/or Sponsor except for allergic/hypersensitivity reactions and any out-of-range laboratory values without clinical correlate which are reversible within 7 days.
- No MTD reached until now
- Overall only 2 SAEs have been observed as related to study medication Example 4

Pharmacokinetics and Pharmacodynamics

After single and multiple doses, EMD 525797 showed a dose-dependent, non-linear PK profile (FIG. 2). After the first 1-hour intravenous infusion, $C_{max}$ of DI17E6 (EMD 525797) was generally reached within 1-2 hours after the start of dosing. The elimination half-life increased with dose as a consequence of EMD 525797 clearance increasing with dose, whereas mean volume of distribution remained constant over the dose range (Table 4).

As in FIG. 2 (table 4) depicted, administration of cohort 2 CRPC patients with 500 mg/each 2 weeks reached serum levels with IC95, whereas patients from cohort 1 with 250 mg/each 2 weeks failed. The serum trough concentration of EMD 525797 in cohort 2, 500 mg/each 2 weeks, is above the $IC_{95}$ and reach the $IC_{99}$ of the non-linear CL pathway (250 mg/each 2 weeks failed).

mg cohort; two patients reverted to seronegative status after two weeks, one patient had no follow-up, and one patient remained seropositive over the entire study period.

Example 5

Circulating Tumor Cells (CTC)

Assessment of circulating tumor cells (CTC) using Cell-Search has been cleared by the Food and Drug Administration as a prognostic factor for patients with metastatic prostate cancer. Several groups have shown that CTC are detected at high frequency in CRPC and are correlated with clinical outcomes (de Bono et al. 2008, Clin Cancer Res, Scher et al. The Lancet 2009).

In FIG. 1 the effect of DI17E6 on circulating tumor cells (CTC) is depicted. Patient No. 2002 from cohort with a dose of 500 mg per each 2 weeks shows a decrease in CTC. Other patients had originally low level of CTC and therefore no significant change after 3 infusions at week 7. This effect was not observed in cohort 1 with 250 mg per each two weeks, where a steep increase can be observed in 5 out of 7 patients at Week 7.

Example 6

Bone Markers

Bone resorption is responsible for the major morbidity in Prostate cancer. Skeletal events are important in the progression of Prostate cancer. Markers to evaluate bone resorption and bone formation were assessed in the study. A pairwise correlation for all markers per cohort was performed and a potential dose effect for cohort II observed.

Bone markers are clustering together in cohort II and not in cohort I. The biological meaning is not completely, but

TABLE 4

| | 250 mg (N = 6) | 500 mg (N = 6) | 1000 mg (N = 6) | 1500 mg (N = 6) |
|---|---|---|---|---|
| $C_{max}$, μg/mL, mean ± SD | 57.1 ± 13.8 | 131.9 ± 22.8 | 376.6 ± 64.1 | 498.8 ± 132.8 |
| $T_{max}$, h, median (range) | 1 (1-5) | 3 (1-5) | 1 (1-4) | 1 (1-8) |
| $C_{min}$, μg/mL, mean ± SD | 2.7 ± 4.1 | 28.0 ± 12.3 | 102.8 ± 28.2 | 150.7 ± 47.4 |
| $V_{ss}$, L, mean ± SD | 4.75 ± 1.19 | 4.35 ± 0.17 | 3.36 ± 0.36 | 4.46 ± 1.22 |
| $AUC_T$ μg/mL * h, mean ± SD | 6694 ± 3746 | 21225 ± 6505 | 68145 ± 12811 | 87535 ± 21575 |
| Ratio_AUC, mean ± SD | 1.42 ± 0.46 | 1.37 ± 0.39 | 1.70 ± 0.36 | 1.70 ± 0.18 |
| Ratio_$C_{max}$, mean ± SD | 1.11 ± 0.17 | 1.21 ± 0.22 | 1.25 ± 0.12 | 1.33 ± 0.18 |

$AUC_T$, area under the concentration-time curve within one complete dosing interval;
$C_{max}$, maximum serum concentration,
$C_{min}$, through serum concentration;
Ratio_AUC, relative area under the curve [$AUC_T$(Dose period3)/$AUC_T$(Dose period 1)];
Ratio_$C_{max}$, relative maxiumum serum concentration [$C_{max}$(Dose period 3)/$C_{max}$(Dose period 1)];
$t_{max}$, time to reach $C_{max}$;
$V_{ss}$, apparent volume of distribution at steady stage.

After multiple doses, DI17E6 (EMD 525797) maximal serum concentrations and exposure accumulated dose-dependently up to a maximum value (dosing period 3/dosing period 1) of 1.33 and 1.70, respectively, at 1500 mg.

In most patients, CTC concentrations remained stable around baseline values (data not shown). In two patients, considerable decreases in CTC concentrations were observed at around 14 and 42 days after the start of treatment, respectively.

Anti-EMD 525797 antibodies were detected in 4 of 25 (16.0%) evaluable patients. All four patients were in the 250 this could indicate a dose effect in relation to the bone markers in the treatment of Prostate cancer with DI-17E6. It could be that DI-17E6 "normalizes" the bone activity so that the bone resorption markers and the bone formation markers are regulated in a more balanced way closer to a normal state than in the disease state. It has been shown that in mCRPC bone resorption markers are often overexpressed. Outstanding biomarkers which can be observed in context with the administration of DI17E6 are ADAMTS-1, STC1, IL6 and IL8.

As in FIG. 7 depicted, two dose levels (250 mg and 500 mg) are compared. The 500 mg dose shows three clusters (box right sight of dose level 2=500 mg) of a pairwise correlation.

Example 7

Change in PSA Level and Pain Score by Treatment with DI17E6

FIGS. 4A and 5A show the change of serum PSA levels in two patients during treatment with 500 mg/each 2 weeks DI17E6.

The level of PSA is related to tumour growth and has a positive correlation with tumor burden. A decrease of more than 50% in the PSA level as compared with the baseline has been proposed as a biological response criterion.

In clinical practice, PSA is measured accurately and easily. Most physicians base their decision about continuing treatment on a general impression of the patients well-being and on their PSA kinetics.

Two patients (see charts from subjects 2001 and 2002) from the 500 mg dose cohort show a more than 8fold decrease of the PSA values during treatment compared to baseline values (FIG. 4A, 5A).

TABLE 5

PSA values from all subjects from screening to week 7.

| patient | screening | w1d1 | w3d15 | w5d29 | w7d43 |
|---|---|---|---|---|---|
| 1002 | 104.4 | 130.5 | 169.7 | 195.3 | 222 |
| 1004 | 5.7 | 5.9 | 11.3 | 8.7 | 6.6 |
| 1005 | 34.3 | 44.7 | 46.6 | 47 | 48.5 |
| 1006 | 1914 | 1622 | 1572 | 1531 | 1448 |
| 1001 | 60.1 | 68.1 | 88.9 | 123.9 | 167.2 |
| 1008 | 472 | 609.5 | 821.5 | | |
| 2001 | 77.5 | 83.3 | 81.5 | 129.6 | 111.3 |
| 2002 | 4774 | 6699 | 6500 | 5943 | 7878 |
| 2005 | 91.1 | 94.3 | 135.6 | 137.9 | 148.66 |
| 2007 | 28.9 | 25 | 33.3 | 40.4 | |
| 2003 | 150.4 | 171.1 | 212.1 | 259.2 | |
| 2009 | 1723 | 1788 | 2194 | 2694 | 3155 |
| 3003 | 83.00 | 84.40 | 102.60 | 108.50 | 109.50 |
| 3004 | 152.40 | 156.90 | 206.30 | 208.50 | 279.60 |
| 3001 | 354.80 | 450.50 | 539.60 | 528.00 | |
| 3005 | 173.00 | 167.50 | 195.70 | 182.10 | 241.00 |
| 3006 | 2273.00 | 2337.00 | 2848.00 | 3430.00 | 3492.00 |
| 3002 | 49.90 | 59.70 | 84.10 | 100.00 | 63.80 |
| 4002 | 346.00 | 426.00 | 432.00 | 555.00 | 547.00 |
| 4003 | 2182.00 | 2495.00 | 2320.00 | 2731.00 | 2668.00 |
| 4004 | 238.00 | 290.00 | 294.00 | 236.00 | 319.00 |
| 4005 | 114.10 | 150.30 | 216.00 | 353.50 | 568.10 |
| 4009 | 1589.00 | 1458.00 | 1342.00 | 1167.00 | 1084.00 |
| 4011 | 481.20 | 534.70 | | 690.40 | 627.40 |

Pain interference was assessed using the Brief Pain Inventory (BPI). BPI was used to evaluate pain interference with the following: (a) general activity, (b) mood, (c) walking ability, (d) normal work, (e) relations with other people, (f) sleep, and (g) enjoyment of life. Total score for pain interference was calculated as: (Mean score of non-missing questions)×(7/number of non-missing questions). If four or more questions were missing, the pain interference total score was set to missing.

The pain score progression during administration is depicted in FIGS. 4B, 5B. It can be seen by comparing with the PSA progression (FIG. 4A, 5A) that during treatment with DI17E6 the improvement pain is correlated with the decrease of the PSA level. The increase of the pain score in FIG. 4B between days 276 and 296 was due to an arthralgia event independent on the drug effect.

Example 8

Decrease of Primary Tumor and Soft Tumor Lesions (Lymph Nodes)

Bone scans and computed tomography scans (CT) were performed to detect stable/response disease. Subjects with progression in bone or CT scan using PCWG2 and RECIST criteria stopped treatment.

Some patients showed a clinically significant decrease in the primary tumor (prostate) and target lesions (lymph nodes). The CT scan illustrating the shrinkage of both primary and target lesions is presented in FIG. 6.

TABLE 6

Patient 2001, 500 mg/q2w, partial remission in the primary tumor and in measurable lesions assessed in CT scans.

| Patient No. 2001 | 17.08.2009 predose | 29.09.2009 | 28.12.2009 | 25.03.2010 |
|---|---|---|---|---|
| Lymph node (LN) inguinal right | 38 × 36 | 38 × 28 | 16 × 13 | 17 × 10 |
| LN retro- | 30 × 19 | 31 × 19 | 16 × 5 | 8 × 3 |
| LN ilical right | 22 × 15 | 24 × 16 | 13 × 4 | 10 × 4 |
| Prostate Primary | 4.7 × 5 cm | | | 3.1 × 3.3 cm |

Response was assessed by CT/MRI scan and documented according to Response Evaluation Criteria in Solid Tumors (RECIST) criteria. At baseline, tumor lesions were categorized as measurable or non-measurable based on the ability to measure the lesion accurately in at least one dimension. Disease progression was defined as at least a 20% increase in the sum of the longest diameter of measurable lesions compared to nadir or the appearance of new lesions.

Secondary efficacy measures were assessed at screening and throughout the study (PSA and pain interference total score) or at week 6 (response assessment), and at 4- or 12-week intervals, respectively, thereafter for patients continuing treatment beyond week 6.

The invention claimed is:
1. A method of treating a patient suffering from castrate-resistant prostate cancer (CRPC), the method comprising administering to the patient an anti-alpha integrin antibody DI17E6, wherein the antibody comprises a variable and constant light chain sequence comprising the amino acid sequence of SEQ ID NO:1 and a variable and constant heavy chain sequence comprising the amino acid sequence of SEQ ID NO:2, DI17E6 in an amount of 500 mg per two weeks for 4-8 months.
2. The method of claim 1, wherein the cancer is metastasizing.
3. The method of claim 2, wherein the cancer is associated with lymph node metastases.
4. The method of claim 2, wherein the cancer is associated with bone metastases.
5. The method of claim 1, wherein the patient experiences a reduction in prostate-specific antigen value within 4-6 months of starting treatment.
6. The method of claim 1, wherein the number of circulating tumor cells (CTC) declines during antibody treatment.
7. The method of claim 1, wherein the patient's prostate was removed before treatment.
8. The method of claim 1, wherein the patient was pretreated with a chemotherapeutic and/or radiation.
9. The method of claim 1, wherein the antibody is administered as monotherapy.
10. The method of claim 1, wherein the patient's CRPC is progressive after chemotherapy.
11. The method of claim 1, wherein the patient is treated after prostatectomy or other prostate cancer related surgery or radiotherapy.
12. The method of claim 1, wherein the method comprises a sequential or simultaneous administration with a hormonal agent.
13. The method of claim 1, wherein the method comprises sequential or simultaneous administration with an cytostatic or cytotoxic agent selected from the group consisting of: a chemotherapeutic agent, radiation, a tyrosine kinase inhibitor, and an angiogenesis inhibitor.
14. The method of claim 13, wherein said tyrosine kinase inhibitor is an anti-ErbB antibody selected from the group consisting of an anti-EGFR antibody, an anti-Her2 antibody, and an anti-Her3 antibody, and said angiogenesis inhibitor is an alpha-v integrin inhibitor.
15. A method of reducing pain in a patient with castrate-resistant prostate cancer (CRPC) accompanied by bone and/or lymph node metastasis, the method comprising administering an effective dose of an anti-alpha integrin antibody DI17E6, wherein the antibody comprises a variable and constant light chain sequence comprising the amino acid sequence of SEQ ID NO:1 and a variable and constant heavy chain sequence comprising the amino acid sequence of SEQ ID NO:2, DI17E6, wherein the effective dose of the antibody is 500 mg administered every two weeks for 4-8 months.

* * * * *

UNITED STATES PATENT AND TRADEMARK OFFICE
CERTIFICATE OF CORRECTION

PATENT NO. : 9,555,110 B2
APPLICATION NO. : 13/984669
DATED : January 31, 2017
INVENTOR(S) : Axel Hoffmann et al.

It is certified that error appears in the above-identified patent and that said Letters Patent is hereby corrected as shown below:

In the Specification

Delete Column 1, Line 19 through Column 2, Line 7.

At Column 8, Line 2, replace "SEQ ID No. 16" with --SEQ ID No. 5--.

At Column 8, Line 4, replace "SEQ ID No. 17" with --SEQ ID No. 6--.

At Column 8, Line 6, replace "SEQ ID No. 18" with --SEQ ID No. 7--.

At Column 8, Line 8, replace "SEQ ID No. 19" with --SEQ ID No. 4--.

At Column 10, Line 35, replace "SEQ ID No." with --SEQ ID No. 5--.

At Column 10, Line 37, replace "SEQ ID No. 17" with --SEQ ID No. 6--.

At Column 10, Line 39, replace "SEQ ID No." with --SEQ ID No. 7--.

At Column 10, Line 41, replace "SEQ ID No. 19" with --SEQ ID No. 4--.

In the Claims

In Claim 1 at Column 31, Line 4, replace "anti-alpha" with --anti-alpha-v--.

In Claim 1 at Column 31, Line 9, delete "DI17E6" after the phrase "SEQ ID NO:2,".

In Claim 15 at Column 32, Line 20, replace "anti-alpha" with --anti-alpha-v--.

In Claim 15 at Column 32, Line 25, delete "DI17E6," after the phrase "SEQ ID NO:2,".

Signed and Sealed this
Sixteenth Day of May, 2017

Michelle K. Lee
*Director of the United States Patent and Trademark Office*